(12) United States Patent
Gregg et al.

(10) Patent No.: US 11,786,373 B2
(45) Date of Patent: Oct. 17, 2023

(54) CARDIAC VALVE DELIVERY DEVICES AND SYSTEMS

(71) Applicant: Cephea Valve Technologies, Inc., Santa Clara, CA (US)

(72) Inventors: Peter Gregg, Santa Cruz, CA (US); Dan Wallace, Santa Cruz, CA (US); Aaron Grogan, Scotts Valley, CA (US); Crissly Crisostomo, Campbell, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 486 days.

(21) Appl. No.: 17/082,554

(22) Filed: Oct. 28, 2020

(65) Prior Publication Data

US 2021/0038386 A1  Feb. 11, 2021

Related U.S. Application Data

(62) Division of application No. 15/573,555, filed as application No. PCT/US2016/032546 on May 13, 2016, now Pat. No. 10,849,746.

(60) Provisional application No. 62/161,747, filed on May 14, 2015.

(51) Int. Cl.
 *A61F 2/24* (2006.01)

(52) U.S. Cl.
 CPC .......... *A61F 2/2436* (2013.01); *A61F 2/2439* (2013.01)

(58) Field of Classification Search
 CPC .... A61F 2/2427; A61F 2/2436; A61F 2/2439; A61B 17/00234; A61B 2017/00243; A61B 2017/00783
 See application file for complete search history.

(56) References Cited

U.S. PATENT DOCUMENTS

| 3,334,629 A | 8/1967 | Cohn |
| 3,409,013 A | 11/1968 | Berry |
| 3,540,431 A | 11/1970 | Mobin-Ubdin |

(Continued)

FOREIGN PATENT DOCUMENTS

| CA | 2859666 A1 | 6/2013 |
| CN | 1338951 A | 3/2002 |

(Continued)

OTHER PUBLICATIONS

Andersen et al.; Transluminal implantation of artificial heart valves. Description of a new expandable aortic valve and Initial results with implantation by catheter technique in closed chest pigs; Euro. Heart J.; 13(5): 704-708; May 1992. cited byapplicant.

(Continued)

*Primary Examiner* — Dianne Dornbusch
(74) *Attorney, Agent, or Firm* — SLEMAN & LUND LLP

(57) ABSTRACT

A delivery device includes a central elongate structure including an annular member at the distal end, a sheath, a plurality of tethers extending through the central elongate structure, a handle, and a control on the handle. The handle is connected to the elongate structure, the sheath, and the plurality of tethers. The control is configured to move the sheath proximally and distally over the central elongate structure. The annular member includes a plurality of pockets extending radially therearound. Each tether includes a feature on a distal end thereof configured to fit within a pocket of the plurality of pockets to hold the tethers in place.

9 Claims, 44 Drawing Sheets

(56) References Cited

U.S. PATENT DOCUMENTS

| | | |
|---|---|---|
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,531,943 A | 7/1985 | Van Tassel et al. |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,909,252 A | 3/1990 | Goldberger |
| 4,917,102 A | 4/1990 | Miller et al. |
| 4,927,426 A | 5/1990 | Dretler |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,258,023 A | 11/1993 | Reger |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,405,377 A | 4/1995 | Cragg |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,183 A | 9/1996 | Nazari |
| 5,554,185 A | 9/1996 | Block et al. |
| 5,571,215 A | 11/1996 | Sterman et al. |
| 5,573,520 A | 11/1996 | Schwartz et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson, IV et al. |
| 5,720,391 A | 2/1998 | Dohm et al. |
| 5,725,552 A | 3/1998 | Kotula et al. |
| 5,733,325 A | 3/1998 | Robinson et al. |
| 5,735,842 A | 4/1998 | Krueger et al. |
| 5,769,812 A | 6/1998 | Stevens et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,957,973 A | 9/1999 | Quiachon et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,984,973 A | 11/1999 | Girard et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,525 A | 2/2000 | Suh et al. |
| 6,042,598 A | 3/2000 | Tsugita et al. |
| 6,042,607 A | 3/2000 | Williamson, IV et al. |
| 6,093,203 A | 7/2000 | Uflacker |
| 6,113,612 A | 9/2000 | Swanson et al. |
| 6,123,723 A | 9/2000 | Konya et al. |
| 6,142,987 A | 11/2000 | Tsugita |
| 6,162,245 A | 12/2000 | Jayaraman |
| 6,165,209 A | 12/2000 | Patterson et al. |
| 6,168,579 B1 | 1/2001 | Tsugita |
| 6,171,327 B1 | 1/2001 | Daniel et al. |
| 6,174,322 B1 | 1/2001 | Schneidt |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,909 B1 | 3/2001 | Hanada et al. |
| 6,214,036 B1 | 4/2001 | Letendre et al. |
| 6,221,006 B1 | 4/2001 | Dubrul et al. |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,309,417 B1 | 10/2001 | Spence et al. |
| 6,312,465 B1 | 11/2001 | Griffin et al. |

(56) References Cited

U.S. PATENT DOCUMENTS

| | | |
|---|---|---|
| 6,319,281 B1 | 11/2001 | Patel |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,368 B1 | 4/2002 | Corcoran et al. |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,411,552 B1 | 6/2002 | Chiba |
| 6,416,510 B1 | 7/2002 | Altman et al. |
| 6,419,696 B1 | 7/2002 | Ortiz et al. |
| 6,425,916 B1 | 7/2002 | Garrison et al. |
| 6,440,152 B1 | 8/2002 | Gainor et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,527,800 B1 | 3/2003 | McGuckin, Jr. et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,656,206 B2 | 12/2003 | Corcoran et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,836 B1 | 3/2004 | Berg et al. |
| 6,712,842 B1 | 3/2004 | Gifford, III et al. |
| 6,712,843 B2 | 3/2004 | Elliott |
| 6,714,842 B1 | 3/2004 | Ito |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,752,828 B2 | 6/2004 | Thornton |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,218 B2 | 9/2004 | Jayaraman |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,037 B2 | 6/2005 | Gainor et al. |
| 6,913,614 B2 | 7/2005 | Marino et al. |
| 6,921,397 B2 | 7/2005 | Corcoran et al. |
| 6,936,058 B2 | 8/2005 | Forde et al. |
| 6,936,067 B2 | 8/2005 | Buchanan |
| 6,945,997 B2 | 9/2005 | Huynh et al. |
| 6,951,571 B1 | 10/2005 | Srivastava |
| 6,953,332 B1 | 10/2005 | Kurk et al. |
| 6,960,220 B2 | 11/2005 | Marino et al. |
| 6,960,224 B2 | 11/2005 | Marino et al. |
| 6,974,464 B2 | 12/2005 | Quijano et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,077,861 B2 | 7/2006 | Spence |
| 7,087,072 B2 | 8/2006 | Marino et al. |
| 7,115,135 B2 | 10/2006 | Corcoran et al. |
| 7,122,020 B2 | 10/2006 | Mogul |
| 7,144,410 B2 | 12/2006 | Marino et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,192,435 B2 | 3/2007 | Corcoran et al. |
| 7,201,772 B2 | 4/2007 | Schwammenthal et al. |
| 7,235,093 B2 | 6/2007 | Gregorich |
| 7,261,732 B2 | 8/2007 | Justino |
| 7,320,704 B2 | 1/2008 | Lashinski et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,402,171 B2 | 7/2008 | Osborne et al. |
| 7,413,563 B2 | 8/2008 | Corcoran et al. |
| 7,445,631 B2 | 11/2008 | Salahieh et al. |
| 7,455,689 B2 | 11/2008 | Johnson |
| 7,566,336 B2 | 7/2009 | Corcoran et al. |
| 7,582,104 B2 | 9/2009 | Corcoran et al. |
| 7,591,848 B2 | 9/2009 | Allen |
| 7,625,364 B2 | 12/2009 | Corcoran et al. |
| 7,632,298 B2 | 12/2009 | Hijlkema et al. |
| 7,658,748 B2 | 2/2010 | Marino et al. |
| 7,691,115 B2 | 4/2010 | Corcoran et al. |
| 7,712,606 B2 | 5/2010 | Salahieh et al. |
| 7,722,666 B2 | 5/2010 | Lafontaine |
| 7,748,389 B2 | 7/2010 | Salahieh et al. |
| 7,749,238 B2 | 7/2010 | Corcoran et al. |
| 7,780,725 B2 | 8/2010 | Haug et al. |
| 7,803,184 B2 | 9/2010 | McGuckin, Jr. et al. |
| 7,803,186 B1 | 9/2010 | Li et al. |
| 7,824,442 B2 | 11/2010 | Salahieh et al. |
| 7,824,443 B2 | 11/2010 | Salahieh et al. |
| 7,896,915 B2 | 3/2011 | Guyenot et al. |
| 7,905,901 B2 | 3/2011 | Corcoran et al. |
| 7,927,351 B2 | 4/2011 | Corcoran et al. |
| 7,972,361 B2 | 7/2011 | Corcoran et al. |

(56) References Cited

U.S. PATENT DOCUMENTS

| | | |
|---|---|---|
| 8,043,368 B2 | 10/2011 | Crabtree |
| 8,057,540 B2 | 11/2011 | Letac et al. |
| 8,092,520 B2 | 1/2012 | Quadri |
| 8,167,935 B2 | 5/2012 | McGuckin, Jr. et al. |
| 8,236,049 B2 | 8/2012 | Rowe et al. |
| 8,317,858 B2 | 11/2012 | Straubinger et al. |
| 8,366,741 B2 | 2/2013 | Chin et al. |
| 8,398,708 B2 | 3/2013 | Meiri et al. |
| 8,425,593 B2 | 4/2013 | Braido et al. |
| 8,444,689 B2 | 5/2013 | Zhang |
| 8,449,599 B2 | 5/2013 | Chau et al. |
| 8,551,132 B2 | 10/2013 | Skridge et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,966 B2 | 11/2013 | Seguin et al. |
| 8,623,074 B2 | 1/2014 | Ryan |
| 8,628,566 B2 | 1/2014 | Eberhardt et al. |
| 8,673,000 B2 | 3/2014 | Tabor et al. |
| 8,685,080 B2 | 4/2014 | White |
| 8,721,708 B2 | 5/2014 | Seguin et al. |
| 8,728,155 B2 | 5/2014 | Montorfano et al. |
| 8,740,962 B2 | 6/2014 | Finch et al. |
| 8,795,356 B2 | 8/2014 | Quadri et al. |
| 8,801,779 B2 | 8/2014 | Seguin et al. |
| 8,845,722 B2 | 9/2014 | Gabbay |
| 8,852,272 B2 | 10/2014 | Gross et al. |
| 8,870,948 B1 | 10/2014 | Erzberger et al. |
| 8,894,702 B2 | 11/2014 | Quadri et al. |
| 8,911,455 B2 | 12/2014 | Quadri et al. |
| 8,956,404 B2 | 2/2015 | Bortlein et al. |
| 8,986,375 B2 | 3/2015 | Garde et al. |
| 8,998,976 B2 | 4/2015 | Gregg et al. |
| 9,011,527 B2 | 4/2015 | Li et al. |
| 9,017,399 B2 | 4/2015 | Gross et al. |
| 9,023,074 B2 | 5/2015 | Theobald et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,060,857 B2 | 6/2015 | Nguyen et al. |
| 9,101,467 B2 | 8/2015 | Eberhardt et al. |
| 9,125,740 B2 | 9/2015 | Morriss et al. |
| 9,132,009 B2 | 9/2015 | Hacohen et al. |
| 9,155,617 B2 | 10/2015 | Carpentier et al. |
| 9,168,130 B2 | 10/2015 | Straubinger et al. |
| 9,168,131 B2 | 10/2015 | Yohanan et al. |
| 9,232,994 B2 | 1/2016 | Miller |
| 9,339,385 B2 | 5/2016 | Glazier et al. |
| 9,387,071 B2 | 7/2016 | Tuval et al. |
| 9,393,110 B2 | 7/2016 | Levi et al. |
| 9,393,112 B2 | 7/2016 | Tuval et al. |
| 9,414,852 B2 | 8/2016 | Gifford, III et al. |
| 9,414,913 B2 | 8/2016 | Beith et al. |
| 9,421,083 B2 | 8/2016 | Eidenschink et al. |
| 9,421,098 B2 | 8/2016 | Gifford et al. |
| 9,439,757 B2 | 9/2016 | Wallace et al. |
| 9,474,605 B2 | 10/2016 | Rowe et al. |
| 9,474,609 B2 | 10/2016 | Haverkost et al. |
| 9,480,556 B2 | 11/2016 | Revuelta et al. |
| 9,480,558 B2 | 11/2016 | Destefano |
| 9,480,563 B2 | 11/2016 | Li |
| 9,486,306 B2 | 11/2016 | Tegels et al. |
| 9,492,273 B2 | 11/2016 | Wallace et al. |
| 9,498,330 B2 | 11/2016 | Solem |
| 9,504,564 B2 | 11/2016 | Nguyen et al. |
| 9,504,568 B2 | 11/2016 | Ryan et al. |
| 9,510,943 B2 | 12/2016 | Mesana et al. |
| 9,554,899 B2 | 1/2017 | Granada et al. |
| 9,561,103 B2 | 2/2017 | Granada et al. |
| 9,579,198 B2 | 2/2017 | Deem et al. |
| 9,655,722 B2 | 5/2017 | Morriss et al. |
| 9,713,523 B2 | 7/2017 | Zacharias et al. |
| 9,883,941 B2 | 2/2018 | Hastings et al. |
| 9,949,824 B2 | 4/2018 | Bonhoeffer et al. |
| 10,004,601 B2 | 6/2018 | Tuval et al. |
| 2001/0007956 A1 | 7/2001 | Letac et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044652 A1 | 11/2001 | Moore |
| 2001/0044656 A1 | 11/2001 | Williamson et al. |
| 2002/0002396 A1 | 1/2002 | Ulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0062135 A1 | 5/2002 | Mazzocchi et al. |
| 2002/0082609 A1 | 6/2002 | Green |
| 2002/0095173 A1 | 7/2002 | Mazzocchi et al. |
| 2002/0120328 A1 | 8/2002 | Pathak et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0074011 A1 | 4/2003 | Gilboa et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199971 A1 | 10/2003 | Tower et al. |
| 2003/0208224 A1 | 11/2003 | Broome |
| 2003/0212429 A1 | 11/2003 | Keegan et al. |
| 2003/0212454 A1 | 11/2003 | Scott et al. |
| 2003/0216774 A1 | 11/2003 | Larson |
| 2003/0225421 A1 | 12/2003 | Peavey et al. |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0060563 A1 | 4/2004 | Rapacki et al. |
| 2004/0082904 A1 | 4/2004 | Hloude et al. |
| 2004/0082967 A1 | 4/2004 | Broome et al. |
| 2004/0087982 A1 | 5/2004 | Eskuri |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0143294 A1 | 7/2004 | Corcoran et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |

(56) References Cited

U.S. PATENT DOCUMENTS

| | | |
|---|---|---|
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225354 A1 | 11/2004 | Allen et al. |
| 2004/0254636 A1 | 12/2004 | Flagle et al. |
| 2005/0033402 A1 | 2/2005 | Cully et al. |
| 2005/0070934 A1 | 3/2005 | Tanaka et al. |
| 2005/0075662 A1 | 4/2005 | Pedersen et al. |
| 2005/0085841 A1 | 4/2005 | Eversull et al. |
| 2005/0085842 A1 | 4/2005 | Versull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283962 A1 | 12/2005 | Boudjemline |
| 2005/0288766 A1 | 12/2005 | Plain et al. |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0116717 A1 | 6/2006 | Marino et al. |
| 2006/0155312 A1 | 7/2006 | Levine et al. |
| 2006/0161249 A1 | 7/2006 | Realyvasquez et al. |
| 2006/0190030 A1 | 8/2006 | To et al. |
| 2006/0195183 A1 | 8/2006 | Navia et al. |
| 2006/0235510 A1 | 10/2006 | Johnson et al. |
| 2006/0247680 A1 | 11/2006 | Amplatz et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265045 A1 | 11/2006 | Shiu et al. |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0088431 A1 | 4/2007 | Bourang et al. |
| 2007/0100440 A1 | 5/2007 | Figulla et al. |
| 2007/0112355 A1 | 5/2007 | Salahieh et al. |
| 2007/0118214 A1 | 5/2007 | Salahieh et al. |
| 2007/0167955 A1 | 7/2007 | Arnault De La Menardiere et al. |
| 2007/0203503 A1 | 8/2007 | Salahieh et al. |
| 2007/0203560 A1 | 8/2007 | Forster et al. |
| 2007/0203575 A1 | 8/2007 | Forster et al. |
| 2007/0244552 A1 | 10/2007 | Salahieh et al. |
| 2007/0255389 A1 | 11/2007 | Oberti et al. |
| 2007/0265656 A1 | 11/2007 | Amplatz et al. |
| 2007/0276324 A1 | 11/2007 | Laduca et al. |
| 2007/0288089 A1 | 12/2007 | Gurskis et al. |
| 2008/0015619 A1 | 1/2008 | Figulla et al. |
| 2008/0033543 A1 | 2/2008 | Gurskis et al. |
| 2008/0082165 A1 | 4/2008 | Wilson et al. |
| 2008/0140189 A1 | 6/2008 | Nguyen et al. |
| 2008/0140191 A1 | 6/2008 | Mathis et al. |
| 2008/0167682 A1 | 7/2008 | Corcoran et al. |
| 2008/0177381 A1 | 7/2008 | Navia et al. |
| 2008/0188928 A1 | 8/2008 | Salahieh et al. |
| 2008/0208328 A1 | 8/2008 | Antocci et al. |
| 2008/0208332 A1 | 8/2008 | Amphere et al. |
| 2008/0221672 A1 | 9/2008 | Lamphere et al. |
| 2008/0234797 A1 | 9/2008 | Styrc |
| 2008/0288054 A1 | 11/2008 | Pulnev et al. |
| 2009/0005863 A1 | 1/2009 | Goetz et al. |
| 2009/0062841 A1 | 3/2009 | Amplatz et al. |
| 2009/0082803 A1 | 3/2009 | Adams et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0287290 A1 | 11/2009 | Macaulay et al. |
| 2009/0306768 A1 | 12/2009 | Quadri |
| 2010/0036479 A1 | 2/2010 | Hill et al. |
| 2010/0049313 A1 | 2/2010 | Alon et al. |
| 2010/0082089 A1 | 4/2010 | Quadri et al. |
| 2010/0094314 A1 | 4/2010 | Hiernlund et al. |
| 2010/0114308 A1 | 5/2010 | Maschke |
| 2010/0121434 A1 | 5/2010 | Paul et al. |
| 2010/0161036 A1 | 6/2010 | Pintor et al. |
| 2010/0191326 A1 | 7/2010 | Alkhatib |
| 2010/0219092 A1 | 9/2010 | Salahieh et al. |
| 2010/0268204 A1 | 10/2010 | Tieu et al. |
| 2010/0280495 A1 | 11/2010 | Paul et al. |
| 2010/0284724 A1 | 11/2010 | Cardia |
| 2010/0298931 A1 | 11/2010 | Quadri et al. |
| 2010/0312333 A1 | 12/2010 | Navia et al. |
| 2011/0004296 A1 | 1/2011 | Lutter et al. |
| 2011/0022157 A1 | 1/2011 | Essinger et al. |
| 2011/0034987 A1 | 2/2011 | Kennedy |
| 2011/0166636 A1 | 7/2011 | Rowe |
| 2011/0218619 A1 | 9/2011 | Benichou et al. |
| 2011/0245911 A1 | 10/2011 | Quill et al. |
| 2011/0257723 A1 | 10/2011 | McNamara |
| 2011/0264198 A1 | 10/2011 | Murray, III et al. |
| 2011/0295363 A1 | 12/2011 | Girard et al. |
| 2011/0301702 A1 | 12/2011 | Rust et al. |
| 2012/0016464 A1 | 1/2012 | Seguin |
| 2012/0059458 A1 | 3/2012 | Buchbinder et al. |
| 2012/0078360 A1 | 3/2012 | Rafiee |
| 2012/0101572 A1 | 4/2012 | Kovalsky et al. |
| 2012/0158129 A1 | 6/2012 | Duffy et al. |
| 2012/0197283 A1 | 8/2012 | Marchand et al. |
| 2012/0197391 A1 | 8/2012 | Alkhatib et al. |
| 2012/0277734 A1 | 11/2012 | Goetz et al. |
| 2013/0041447 A1 | 2/2013 | Erb et al. |
| 2013/0041458 A1 | 2/2013 | Lashinski et al. |
| 2013/0197629 A1 | 8/2013 | Gainor et al. |
| 2013/0253643 A1 | 9/2013 | Rolando et al. |
| 2013/0261737 A1 | 10/2013 | Costello |
| 2013/0282110 A1 | 10/2013 | Schweich, Jr. et al. |
| 2013/0282114 A1 | 10/2013 | Schweich, Jr. et al. |
| 2013/0304197 A1 | 11/2013 | Buchbinder et al. |
| 2013/0310923 A1 | 11/2013 | Kheradvar et al. |
| 2013/0331931 A1 | 12/2013 | Gregg et al. |
| 2014/0005771 A1 | 1/2014 | Braido et al. |
| 2014/0005775 A1 | 1/2014 | Alkhatib et al. |
| 2014/0005778 A1 | 1/2014 | Buchbinder et al. |

(56) References Cited

U.S. PATENT DOCUMENTS

| | | |
|---|---|---|
| 2014/0012368 A1 | 1/2014 | Sugimoto et al. |
| 2014/0012374 A1 | 1/2014 | Rankin |
| 2014/0052237 A1 | 2/2014 | Lane et al. |
| 2014/0052241 A1 | 2/2014 | Harks et al. |
| 2014/0052244 A1 | 2/2014 | Rolando et al. |
| 2014/0067037 A1 | 3/2014 | Fargahi |
| 2014/0067048 A1 | 3/2014 | Chau et al. |
| 2014/0081383 A1 | 3/2014 | Eberhardt et al. |
| 2014/0107665 A1 | 4/2014 | Shellenberger et al. |
| 2014/0128726 A1 | 5/2014 | Quill et al. |
| 2014/0180391 A1 | 6/2014 | Dagan et al. |
| 2014/0214157 A1 | 7/2014 | Bortlein et al. |
| 2014/0214159 A1 | 7/2014 | Vidlund et al. |
| 2014/0222136 A1 | 8/2014 | Geist et al. |
| 2014/0236278 A1 | 8/2014 | Argentine et al. |
| 2014/0243954 A1 | 8/2014 | Shannon |
| 2014/0249622 A1 | 9/2014 | Carmi et al. |
| 2014/0257476 A1 | 9/2014 | Montorfano et al. |
| 2014/0277390 A1 | 9/2014 | Ratz et al. |
| 2014/0277563 A1 | 9/2014 | White |
| 2014/0303718 A1 | 10/2014 | Tegels et al. |
| 2014/0316518 A1 | 10/2014 | Kheradvar et al. |
| 2014/0324164 A1 | 10/2014 | Gross et al. |
| 2014/0330368 A1 | 11/2014 | Gloss et al. |
| 2014/0379076 A1 | 12/2014 | Vidlund et al. |
| 2015/0025623 A1 | 1/2015 | Granada et al. |
| 2015/0039083 A1 | 2/2015 | Rafiee |
| 2015/0045881 A1 | 2/2015 | Lim |
| 2015/0094802 A1 | 4/2015 | Buchbinder et al. |
| 2015/0112430 A1 | 4/2015 | Creaven et al. |
| 2015/0119637 A1 | 4/2015 | Alvarez et al. |
| 2015/0135506 A1 | 5/2015 | White |
| 2015/0142100 A1 | 5/2015 | Morriss et al. |
| 2015/0157455 A1 | 6/2015 | Hoang et al. |
| 2015/0157457 A1 | 6/2015 | Hacohen |
| 2015/0173897 A1 | 6/2015 | Raanani et al. |
| 2015/0223773 A1 | 8/2015 | John et al. |
| 2015/0302634 A1 | 10/2015 | Florent et al. |
| 2015/0351903 A1 | 12/2015 | Morriss et al. |
| 2015/0351904 A1 | 12/2015 | Cooper et al. |
| 2016/0038280 A1 | 2/2016 | Morriss et al. |
| 2016/0089234 A1 | 3/2016 | Gifford, III |
| 2016/0151153 A1 | 6/2016 | Sandstrom et al. |
| 2016/0158000 A1 | 6/2016 | Granada et al. |
| 2016/0158003 A1 | 6/2016 | Wallace et al. |
| 2016/0166384 A1 | 6/2016 | Olson et al. |
| 2016/0310267 A1 | 10/2016 | Zeng et al. |
| 2016/0310269 A1 | 10/2016 | Braido et al. |
| 2017/0035569 A1 | 2/2017 | Deem et al. |
| 2017/0042675 A1 | 2/2017 | Freudenthal |
| 2017/0049571 A1 | 2/2017 | Gifford, III |
| 2017/0209261 A1 | 7/2017 | Bortlein et al. |
| 2017/0209269 A1 | 7/2017 | Conklin |
| 2017/0231762 A1 | 8/2017 | Quadri et al. |
| 2017/0245991 A1 | 8/2017 | Granada et al. |
| 2017/0325941 A1 | 11/2017 | Wallace et al. |
| 2017/0325948 A1 | 11/2017 | Wallace et al. |
| 2017/0354499 A1 | 12/2017 | Granada et al. |
| 2018/0000580 A1 | 1/2018 | Wallace et al. |
| 2018/0206983 A1 | 7/2018 | Noe et al. |
| 2018/0206984 A1 | 7/2018 | Noe et al. |
| 2018/0206985 A1 | 7/2018 | Noe et al. |
| 2018/0206986 A1 | 7/2018 | Noe et al. |
| 2018/0296341 A1 | 10/2018 | Noe et al. |
| 2019/0201196 A1 | 7/2019 | Granada et al. |
| 2019/0247188 A1 | 8/2019 | Wallace et al. |

FOREIGN PATENT DOCUMENTS

| | | |
|---|---|---|
| EP | 0409929 | 1/1991 |
| EP | 0409929 B1 | 1/1991 |
| EP | 0819013 | 1/1998 |
| EP | 0819013 B1 | 1/1998 |
| EP | 0937439 | 8/1999 |
| EP | 0937439 B1 | 8/1999 |
| EP | 1042045 | 10/2000 |
| EP | 1042045 B1 | 10/2000 |
| EP | 1057459 A1 | 12/2000 |
| EP | 1057460 A1 | 12/2000 |
| EP | 1059894 | 12/2000 |
| EP | 1059894 B1 | 12/2000 |
| EP | 1078610 | 2/2001 |
| EP | 1078610 B1 | 2/2001 |
| EP | 1229864 | 8/2002 |
| EP | 1229864 B1 | 8/2002 |
| EP | 1340473 A2 | 9/2003 |
| EP | 1356793 A2 | 10/2003 |
| EP | 1430853 A2 | 6/2004 |
| EP | 1469797 | 10/2004 |
| EP | 1469797 B1 | 11/2005 |
| EP | 1600121 A1 | 11/2005 |
| EP | 1616531 A2 | 1/2006 |
| EP | 1819304 A2 | 8/2007 |
| EP | 1849440 A1 | 10/2007 |
| EP | 2124826 | 12/2009 |
| EP | 2654624 A1 | 10/2013 |
| EP | 2124826 B1 | 7/2014 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9836790 A1 | 8/1998 |
| WO | 9857599 A2 | 12/1998 |
| WO | 9944542 A2 | 9/1999 |
| WO | 0009059 A2 | 2/2000 |
| WO | 0044308 A2 | 8/2000 |
| WO | 200044313 A1 | 8/2000 |
| WO | 0067661 A2 | 11/2000 |
| WO | 0105331 A1 | 1/2001 |
| WO | 0135870 A1 | 5/2001 |
| WO | 0164137 A1 | 9/2001 |
| WO | 0236048 A1 | 5/2002 |
| WO | 2002041789 A2 | 5/2002 |
| WO | 02100297 A2 | 12/2002 |
| WO | 2003003943 A2 | 1/2003 |
| WO | 2003003949 A2 | 1/2003 |
| WO | 03011195 A2 | 2/2003 |
| WO | 03015851 A1 | 2/2003 |
| WO | 2003030776 A2 | 4/2003 |
| WO | 03094797 A1 | 11/2003 |
| WO | 2004014256 A1 | 2/2004 |
| WO | 2004019811 A2 | 3/2004 |
| WO | 2004026117 A2 | 4/2004 |
| WO | 2004041126 A1 | 5/2004 |
| WO | 2004047681 A1 | 6/2004 |
| WO | 2004066876 A1 | 8/2004 |
| WO | 2004082536 A1 | 9/2004 |
| WO | 2005037361 A2 | 4/2005 |
| WO | 2005084595 A1 | 9/2005 |
| WO | 2005087140 A1 | 9/2005 |
| WO | 2009072122 A1 | 6/2009 |
| WO | 2009108615 A1 | 9/2009 |
| WO | 2009132187 A1 | 10/2009 |
| WO | 2009137755 A2 | 11/2009 |
| WO | 2010057262 A1 | 5/2010 |
| WO | 2010141847 A1 | 12/2010 |
| WO | 2011057087 A1 | 5/2011 |
| WO | 2011081997 A1 | 7/2011 |
| WO | 2012161786 A1 | 11/2012 |
| WO | 2013158608 A1 | 10/2013 |
| WO | 2013158613 A1 | 10/2013 |
| WO | 2014121280 A2 | 8/2014 |
| WO | 2014144247 A1 | 9/2014 |
| WO | 2015127283 A1 | 8/2015 |
| WO | 2016168609 A1 | 10/2016 |
| WO | 2016183523 A1 | 11/2016 |
| WO | 2017035002 A1 | 3/2017 |
| WO | 2017035434 A1 | 3/2017 |

(56) References Cited

FOREIGN PATENT DOCUMENTS

| WO | 2017122109 A1 | 7/2017 |
|---|---|---|
| WO | 2017167759 A1 | 10/2017 |

OTHER PUBLICATIONS

Atwood et al.; Insertion of Heart Valves by Catheterization; Project Supervised by Prof. S. Muftu of Northeastern University, May 2002: pp. 36-40.

Bodnar et al. Replacement Cardiac Valves; (Chapter 13) Extinct cardiac valve prostheses. Pergamon Publishing Corporation. New York, Aug. 1991: pp. 307-322.

Boudjemline et al. Percutaneous implantation of a biological valve in the aorta to treat aortic valve insufficiency—a sheep study.f Med Sci. Monit; Apr. 2002; vol. 8, No. 4: BR113-116.

Boudjemline et al. "Percutaneous implantation of a valve in the descending aorta in lambs." Euro. Heart J; Jul. 2002; 23: 1045-1049.

Boudjemline et al. "Percutaneous pulmonary valve replacement in a large right ventricular outflow tract: an experimental study." Journal of the American College of Cardiology; Mar. 2004; vol. 43(6): 1082-1087.

Boudjemline et al. "Percutaneous valve insertion: A new approach?" J. of Thoracic and Cardio. Surg; Mar. 2003; 125(3): 741-743.

Boudjemline et al. "Steps Toward Percutaneous Aortic Valve Replacement." Circulation; Feb. 2002; 105: 775-778.

Cribier et al. "Early Experience with Percutaneous Transcatheter Implantation of Heart Valve Prosthesis for the Treatment of End-Stage Inoperable Patients with Calcific Aortic Stenosis." J. of Am. Coli. of Cardio; Feb. 2004; 43(4): 698-703.

Cribier et al. "Percutaneous Transcatheter Implantation of an Aortic Valve Prosthesis for Calcific Aortic Stenosis: First Human Case." Percutaneous Valve Technologies, Inc. 2002: 16 pages (year of pub. sufficiently earlier than effective US filedand any foreign priority date).

Cribier et al. "Percutaneous Transcatheter Implantation of an Aortic Valve Prosthesis for Calcific Aortic Stenosis: First Human Case." (slide presentation); TCT 2002 (conference); 16 pgs.; Washington D.C.; Sep. 24-28, 2002.

Ferrari et al. "Percutaneous transvascular aortic valve replacement with self expanding stent-valve device." Poster from the presentation given at SMIT 2000, 12th International Conference. 1 pg. Sep. 5, 2000.

Hijazi "Transcatheter Valve Replacement: A New Era of Percutaneous Cardiac Intervention Begins." J. of Am. College of Cardia; Mar. 2004; 43(6): 1088-1089.

Huber et al. "Do valved stents compromise coronary flow?" European Journal of Cardio-thoracic Surgery; May 2004; vol. 25: 754-759.

Knudsen et al. "Catheter-implanted prosthetic heart valves." Int'l J. of Art. Organs; May 1993; 16(5): 253-262.

Kort et al. "Minimally invasive aortic valve replacement: Echocardiographic and clinical results." Am. Heart J; Sep. 2001; 142(3): 476-481.

Love et al. The Autogenous Tissue Heart Valve: Current Stat. Journal of Cardiac Surgery; Dec. 1991; 6(4): 499-507.

Lutter et al. "Percutaneous aortic valve replacement: An experimental study. I. Studies on implantation." J. of Thoracic and Cardio. Surg; Apr. 2002; 123(4 ): 768-776.

Moulopoulos et al. "Catheter-Mounted Aortic Valves." Annals of Thoracic Surg; May 1971; 11(5): 423-430.

Paniagua et al. "Percutaneous heart valve in the chronic in vitro testing model." Circulation; Sep. 2002; 106: e51-e52.

Paniagua et al. Heart Watch (2004). Texas Heart Institute. Spring (March) 2004 Edition: 8 pages.

Pavcnik et al. "Percutaneous bioprosthetic veno valve: A long-term study in sheep." J. of Vascular Surg; Mar. 2002; 35(3): 598-603.

Phillips et al. "A Temporary Catheter-Tip Aortic Valve: Hemodynamic Effects on Experimental Acute Aortic Insufficiency." Annals of Thoracic Surg; Feb. 1976; 21 (2): 134-136.

Sochman et al. "Percutaneous Transcatheter Aortic Disc Valve Prosthesis Implantation: A Feasibility Study." Cardiovasc. Lntervent. Radiol; Sep.-Oct. 2000; 23: 384-388.

Solvay; Novel revivent(tm) Myocardial anchoring system from bioVentrix uses solvay's zeniva@ PEEK in tether component; 3 pages retrieved from the internet (http://www.solvay.com/en/media/press_release/20131205•novel-revivent-myocardial-anchoring-system-bioventrix-uses-zenivapeek.html); (Press Release); on Aug. 10, 2017.

Stuart, M. "In Heart Valves, a Brave, New Non-Surgical World." Start-Up; Feb. 2004: 9-17.

Vahanian et al. "Percutaneous Approaches to Valvular Disease." Circulation; Apr. 2004; 109:1572-1579.

Van Herwerden et al., "Percutaneous valve implantation: back to the future?" Euro. Heart J; Sep. 2002; 23(18): 1415-1416.

Zhou et al. "Self-expandable valved stent of large size: off-bypass implantation in pulmonary position." Eur. J. Cardiothorac; Aug. 2003; 24: 212-216.

Extended European Search Report including Written Opinion for Application No. EP16793655.8 dated Jan. 15, 2019, pp. 1-8.

Cribier et al. "Percutaneous Transcatheter Implantation of an Aortic Valve Prosthesis for Calcific Aortic Stenosis: First Human Case Description." Circulation; Dec. 2002; 106: 3006-3008.

Hijazi "Transcatheter Valve Replacement: A New Era of Percutaneous Cardiac Intervention Begins." J. of Am. College of Cardio; Mar. 2004; 43(6): 1088-1089.

Love et al. The Autogenous Tissue Heart Valve: Current Stat.f Journal of Cardiac Surgery; Dec. 1991; 6(4): 499-507.

Sochman et al. "Percutaneous Transcatheter Aortic Disc Valve Prosthesis Implantation: A Feasibility Study." Cardiovasc. Intervent. Radiol; Sep.-Oct. 2000; 23: 384-388.

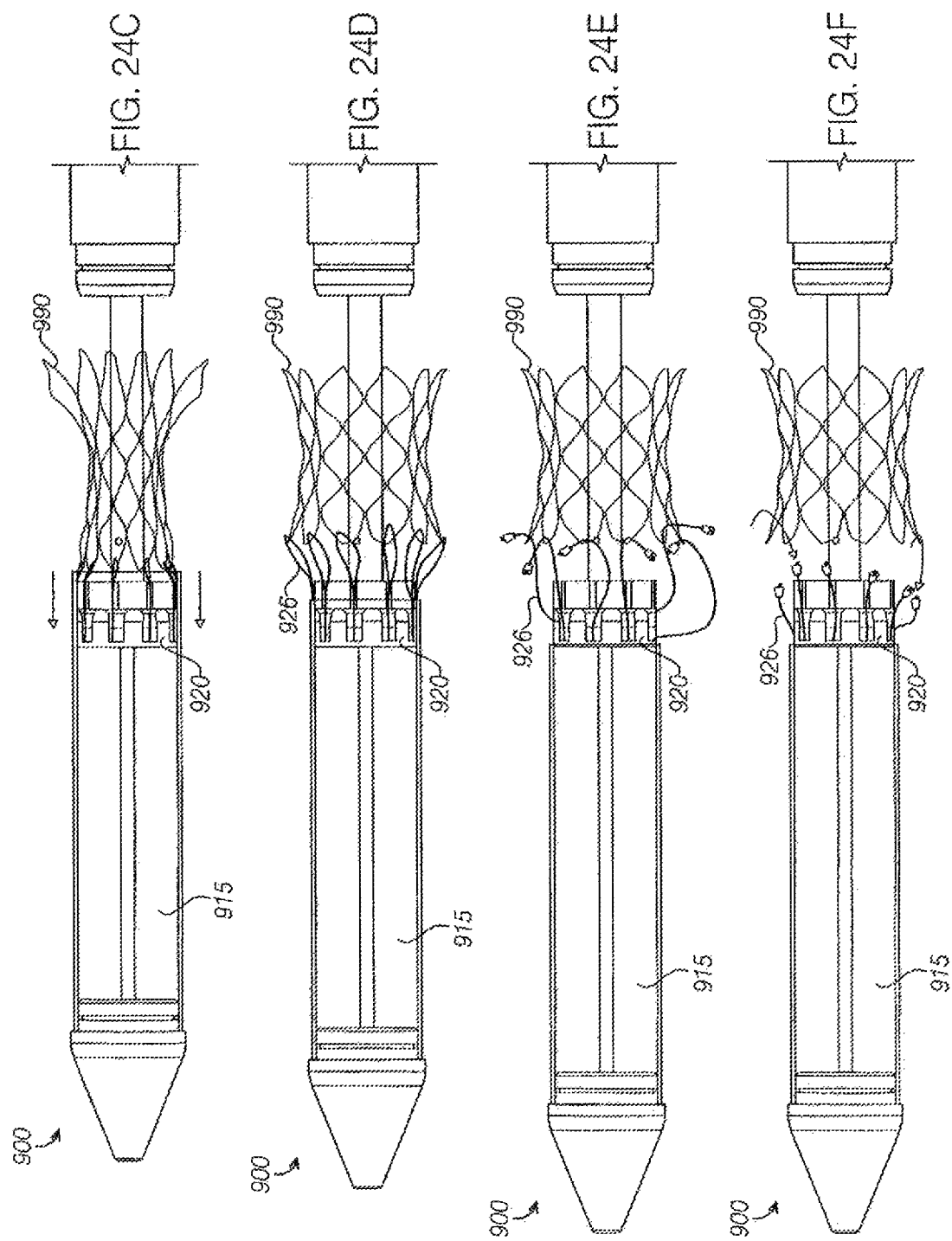

CARDIAC VALVE DELIVERY DEVICES AND SYSTEMS

CROSS REFERENCE TO RELATED APPLICATIONS

This application is a divisional application of U.S. application Ser. No. 15/573,555, filed on Nov. 13, 2017, which application is a national phase entry under 35 U.S.C. § 371 of International Application No. PCT/US2016/032546, filed on May 13, 2016, which claims the benefit of the filing date of U.S. Provisional Patent Application No. 62/161,747, filed May 14, 2015, titled "CARDIAC VALVE DELIVERY DEVICES AND SYSTEMS," the disclosures of which are hereby incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to the treatment of cardiac valve disorders, such as mitral valve replacement, using minimally invasive techniques. In particular, this application is directed towards devices for delivering and placing replacement mitral valves.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Prosthetic valve replacement procedures can be difficult, and various factors are generally taken into account when placing the valve. First, the prosthetic valve should be placed at the same or very nearly the same angle as the native valve. A valve that is off axis could cause turbulent blood flow and/or potential para-valvular leaks. Second, the prosthetic valve should ideally have concentricity. This means that the valve is placed in the same center as the native valve. An off center deployment or valve placement could affect the mechanism of neighboring valves or the heart's conductive system. Finally, the prosthetic valve should be at the proper depth within the patient's heart with respect to the location of the native valve, as otherwise, the prosthetic valve may interfere with the conductive nature of the heart as well.

A safe and efficient delivery system and method for replacement of a cardiac valve that addresses some or all of these concerns is described herein.

SUMMARY OF THE DISCLOSURE

In general, in one embodiment, a delivery device includes a central elongate structure, a sheath configured to slide over the central elongate structure, a plurality of tethers extending through the central elongate structure, a handle, and a control on the handle configured to move the sheath proximally and distally over the central elongate structure. The central elongate structure includes an annular member at a distal end. The handle is connected to the elongate structure, the sheath, and the plurality of tethers. The annular member includes a plurality of pockets extending radially therearound. Each tether includes a feature on a distal end thereof configured to fit within a pocket of the plurality of pockets to hold the tether in place.

This and other embodiments can include one or more of the following features. The feature can be a cone or a sphere. The feature can be radiopaque. The handle can further include a locking mechanism configured to prevent the control from moving the sheath past a set distance, thereby preventing the features from releasing from the pockets. The locking mechanism can be releasable so as to allow the sheath to move past the set distance to release the features from the pockets. The handle can further include a tether controller configured to provide tension or release tension to each of the plurality of tethers. The handle can further include a tether lock having an open and closed position configured to prevent further loosening or tensioning of the tether when the tether lock is in the closed position. The handle can further include a secondary release knob coupled to the tether controller for allowing the plurality of tethers to be released at their proximal ends. The delivery device can further include a ratcheting assembly configured to prevent forward and back driving of the tether controller. The ratcheting assembly can include a plurality of ratchets coupling the tether controller and the secondary release knob, two beads symmetrically disposed in two channels within the secondary release knob, and three wells adjacent to the bottom of each of the two channels such that only one well is exposed to the bottom of each of the two channels at any one time. The two beads can be maintained at the bottom of the two channels with corresponding springs, and tension to the two beads may be released with corresponding actuators. A location of each bead in one of the three wells of each channel can correspond to limiting tether controller movement in one direction, limiting tether controller movement in an opposite direction, or allowing the tether controller to move in the first or the second direction. The delivery device can further include a series of magnetic strips along one side of the device. The delivery device can further include a grasper that is configured to magnetically couple to the delivery device through the series of magnetic strips. The grasper can include a coupling aperture adapted to couple to a support arm and a grasper knob that when turned is adapted to move the delivery device in an axial direction for placing a prosthetic valve. The delivery device can further include an outer sheath configured to cover a distal portion of the delivery device for maintaining an incision site during a prosthetic valve placement procedure. The outer sheath can further include an annular groove at its distal end for coupling to an incision site boundary when the incision site boundary is cinched together. The delivery can further include a prosthetic valve loading aid for placing the prosthetic valve into the sheath.

In general, in one embodiment, a method of delivering a prosthetic mitral valve includes: (1) extending a prosthetic delivery device into a heart with the prosthetic mitral valve collapsed within a sheath of the delivery device; (2) pulling the sheath proximally to expose at least a distal anchor of the prosthetic valve, thereby allowing the distal anchor to self-expand to an expanded annular configuration on a first side of the mitral valve annulus; (3) pulling the valve proximally to seat the distal anchor in the expanded annular configuration against a mitral valve annulus; (4) loosening a plurality of tethers of the delivery device so as to allow the proximal anchor to self-expand to an expanded annular configuration on a second side of the mitral valve annulus, the expansion of the proximal anchor causing the proximal anchor to move towards the distal anchor and capture tissue of the mitral valve annulus between the proximal anchor and the distal anchor; (5) pulling the sheath further proximally to allow the tethers to release from the proximal anchor; and (6) removing the delivery device from the heart.

This and other embodiments can include one or more of the following features. The step of pulling the sheath further proximally can release distal ends of the tethers. The method can further include releasing a proximal end of at least one tether if a distal end of the at least one tether becomes tangled. Distal ends of the tethers can be configured to fit within pockets of the delivery device, and the step of pulling the sheath further proximally can release the distal ends of the tethers. The distal ends of the tethers can include enlarged features configured to fit within the pockets. The enlarged features can be cones or spheres. The method can further include: (1) tightening the plurality of tethers to re-collapse the proximal anchor before the step of pulling the sheath further proximally; (2) moving the distal anchor to a new position against the mitral valve annulus; and (3) re-loosening the plurality of tethers so as to allow the proximal anchor to self-expand to an expanded annular configuration on a second side of the mitral valve annulus, the expansion of the proximal anchor causing the proximal anchor to move towards the distal anchor and capture tissue of the mitral valve annulus between the proximal anchor and the distal anchor.

In general, in one embodiment, a method of delivering a prosthetic mitral valve includes: (1) extending a prosthetic delivery device into a heart with the prosthetic mitral valve collapsed within a sheath of the delivery device; (2) sliding the sheath to expose at least a proximal anchor of the prosthetic valve and allowing the proximal anchor to self-expand to an expanded annular configuration on a first side of the mitral valve annulus; (3) allowing a distal anchor of the prosthetic valve to self-expand on a second side of the mitral valve annulus after allowing the proximal anchor to self-expand, the expansion of the distal anchor causing the distal anchor to move towards the proximal anchor and capture tissue of the mitral valve annulus between the proximal anchor and the distal anchor; and (4) removing the delivery device from the heart.

This and other embodiments can include one or more of the following features. Sliding the sheath can include sliding the sheath distally. Sliding the sheath to expose at least a proximal anchor of the prosthetic valve can allow the proximal anchor to self-expand to an expanded annular configuration. Allowing the distal anchor to self-expand can include loosening a plurality of tethers of the delivery device that are coupled to the distal anchor.

In general, in one embodiment, a method of delivering a prosthetic mitral valve includes: (1) extending a prosthetic delivery device into a heart with the prosthetic mitral valve collapsed within a proximal sheath and a distal sheath of the delivery device, wherein the distal sheath is configured to telescope over a portion of the proximal sheath; (2) sliding the proximal sheath proximally to expose at least a proximal anchor of the prosthetic valve and allowing the proximal anchor to self-expand to an expanded annular configuration on a first side of the mitral valve annulus; (3) allowing a distal anchor of the prosthetic valve to self-expand on a second side of the mitral valve annulus after allowing the proximal anchor to self-expand by extending the distal sheath, the expansion of the distal anchor causing the distal anchor to move towards the proximal anchor and capture tissue of the mitral valve annulus between the proximal anchor and the distal anchor; and (4) removing the delivery device from the heart.

This and other embodiments can include one or more of the following features. Sliding the proximal sheath to expose at least a proximal anchor of the prosthetic valve can allow the proximal anchor to self-expand to an expanded annular configuration after loosening a plurality of tethers of the delivery device that are coupled to the proximal anchor. Allowing the distal anchor of the prosthetic valve to self-expand can include sliding the distal sheath in a distal direction. The plurality of tethers can further be tensioned to completely free the plurality of tethers from the proximal anchor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 24C shows the distal inner sheath of the delivery device of FIG. 24A extended in a position where proximal end petals are deployed.

FIG. 24D shows the distal inner sheathe extend at an even more distal position relative to FIG. 24C such that an entire prosthetic valve has been deployed.

FIG. 24E shows the distal inner sheath of FIG. 24A extended in the farthest distal end position such that pockets of a tether retainer are exposed and allow the tether ends to be freed.

FIG. 24F shows the tether ends being retracted to allow the delivery device now to be removed.

DETAILED DESCRIPTION

The delivery devices described herein can be used to deliver and deploy a wide variety of replacement heart valves, such as prosthetic valves adapted to be minimally invasively delivered. Exemplary prosthetic valves that can be delivered and deployed include the expandable prosthetic valves described in application Ser. No. 14/677,320, filed Apr. 2, 2015, in U.S. Pat. No. 8,870,948, and in International Patent Application filed May 13, 2016, titled "REPLACEMENT MITRAL VALVES," and in U.S. patent application Ser. No. 14/677,320, filed Apr. 2, 2015, titled "REPLACEMENT CARDIAC VALVES AND METHODS OF USE AND MANUFACTURE," all of which are incorporated by reference herein. For example, the delivery devices herein are configured to be able to delivery and deploy a replacement heart valve, such as a mitral valve, with distal and proximal anchors.

Replacement heart valves can be collapsed into a delivery configuration so they can fit within the described delivery devices. The replacement heart valves can be delivered to the treatment site within the delivery device and then deployed from the delivery device. The delivery device can be configured such that the distal and proximal anchors can be sequentially deployed as desired from a collapsed configuration to an expanded configuration.

If necessary, the replacement valves can be repositioned, re-sheathed (partially or completely) if necessary, and then re-deployed.

In methods of use, the mitral valve prosthesis can be delivered using one of the delivery devices described herein to a cardiac valve orifice, such as the mitral valve, by using minimally invasive techniques to access the cardiac valve. Access routes and procedures are known, such as making small incisions in the patient's body and passing the prosthesis through the apex of the heart to, for example, a mitral valve. This can be referred to as the transatrial delivery approach. In such a transatrial delivery system for a mitral valve replacement, the distal-most anchor is delivered to the ventricle while the proximal-most anchor is delivered to the atrium. An additional exemplary access route includes delivering the valve through the venous system and into the left atrium via a transseptal puncture. A transseptal approach can impart size limitations on the delivery and thus the delivery profile of the replacement heart valve. Additionally, a transseptal approach can also impart certain flexibility requirements on the replacement heart valve. For the transseptal delivery system for mitral valve replacement, the distal-most anchor is delivered to the atrium while the proximal-most anchor is delivered to the ventricle.

Figure 1:
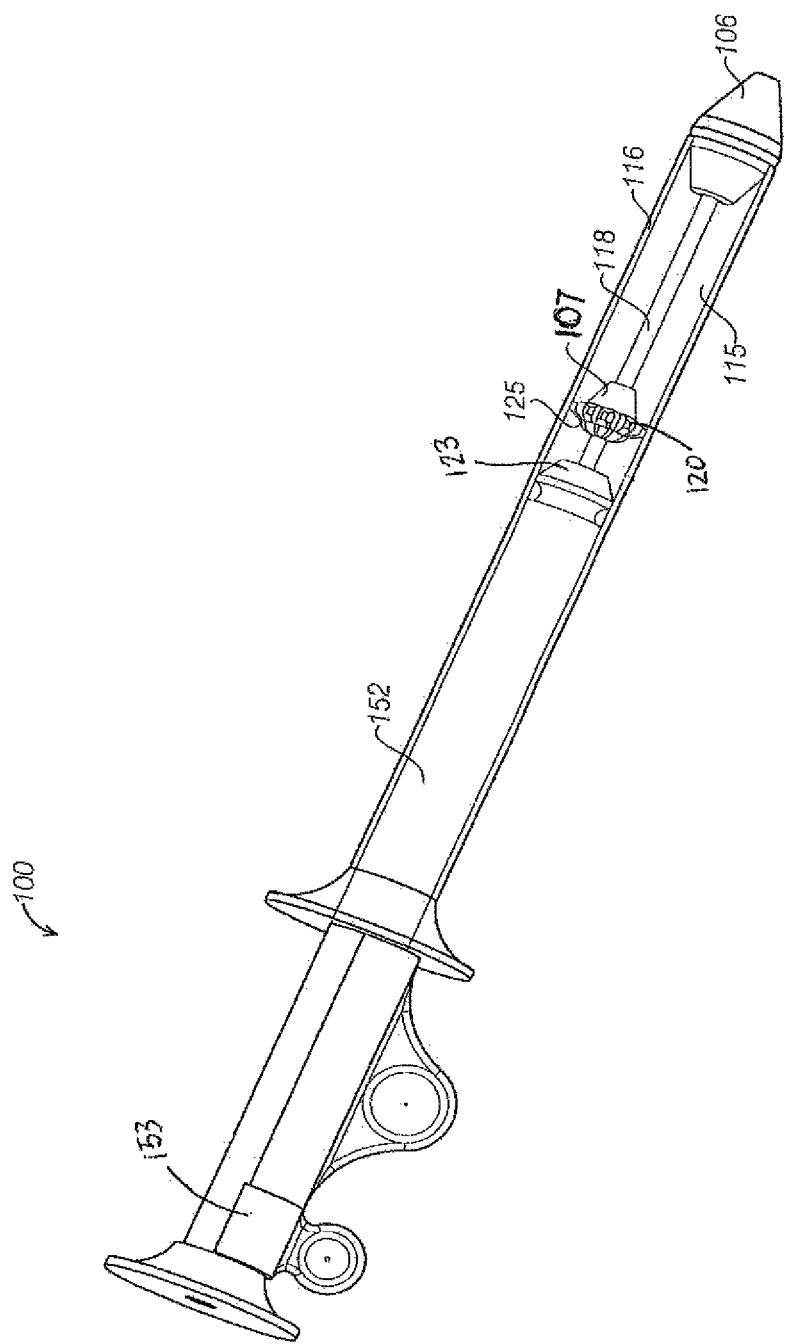
FIG. 1 shows an exemplary prosthetic valve delivery device.

FIG. 1 illustrates an exemplary delivery device 100 that is configured to deliver and deploy a mitral valve prosthesis. The delivery device 100 allows self-expansion of a distal portion of the prosthesis, such as a distal anchor, and controlled deployment of a proximal portion of the prosthesis, such as a proximal anchor. The delivery device 100 includes a central control assembly that includes a central hub 107, which has a lumen extending therethrough. Disposed within and secured within the lumen of the central hub 107 is central stem 118, which extends further distally than the central hub 107, and whose distal region is coupled to nosecone 106. The central control assembly further includes a retaining member 120 secured to the central stem 118 for controlling expansion of the valve prosthesis. Retaining member 120 is configured to interact with a proximal region of the prosthesis (not shown for clarity) and, with the use of sheath 116 as described below, facilitate a controlled deployment of the proximal region of the prosthesis.

Delivery device 100 further includes an outer sheath 116 coupled to sheath control 152. The central control assembly is disposed within sheath 116, and the system is configured so that sheath 116 can be axially moved (proximally and distally) relative to the central control assembly. The distal region 123 of central hub 107, the proximal end of nosecone 106, and the inner surface of sheath 116 define a prosthesis delivery region 115, which is configured to receive and retain therein a prosthesis in a collapsed configuration for delivery.

While the prosthesis is not shown for clarity, in this configuration of the delivery device, the expandable prosthesis would be in a collapsed configuration inside delivery region 115 due to the radial constraint provided by sheath 116. When collapsed, the proximal portion of the prosthesis interacts with, e.g. is attached to, raised elements 125 of retaining member 120. The proximal portion of the prosthesis can include a plurality of self-expandable cells, arcs, or arches (generally referred to herein as cells), such as those features described in application Ser. No. 14/677,320, U.S. Pat. No. 8,870,948, and International Patent Application filed May 13, 2016 and titled "REPLACEMENT MITRAL VALVES." The cells of the proximal portion of the prosthesis (e.g., the proximal anchor), when collapsed, interface with raised elements 125 such that they are looped around raised elements 125. Raised elements 125 project radially outward, extending further radially than valleys 119, which are in between adjacent raised elements 125 and whose configuration is defined by the configuration of the projecting raised elements 125. The raised elements 125 are configured and sized so that when sheath 116 is positioned over the raised elements 125 (i.e., is disposed radially outwardly relative thereto), the space between the inner surface of sheath 116 and the radially outermost surface of raised elements 125 does not allow the cells of the proximal portion of the prosthesis to pass through the space. Raised elements 125 and sheath 116 are therefore sized and configured to maintain the proximal-most portions of the prosthesis proximal to raised elements 125 while the rest of the prosthesis is positioned distal to the raised elements 125. This prevents the proximal portion of the prosthesis from expanding sooner than desired as the sheath is being retracted proximally during deployment of the prosthesis.

The sheath 116 and raised elements 125 are also sized and configured to allow the self-expandable proximal portion of the valve prosthesis to expand radially outward only after the distal end of the sheath 116 has been retracted far enough proximally relative to raised elements 125. Upon removal of sheath lock 153, sheath 116 can be retracted proximally relative to central control assembly to expose the prosthesis and allow for self-expansion. That is, when the distal end of sheath 116 is retracted proximally past raised regions 125, the expandable proximal portion of the prosthesis will expand to its expanded configuration since the radially constraint of the sheath has been removed.

Figure 2A:
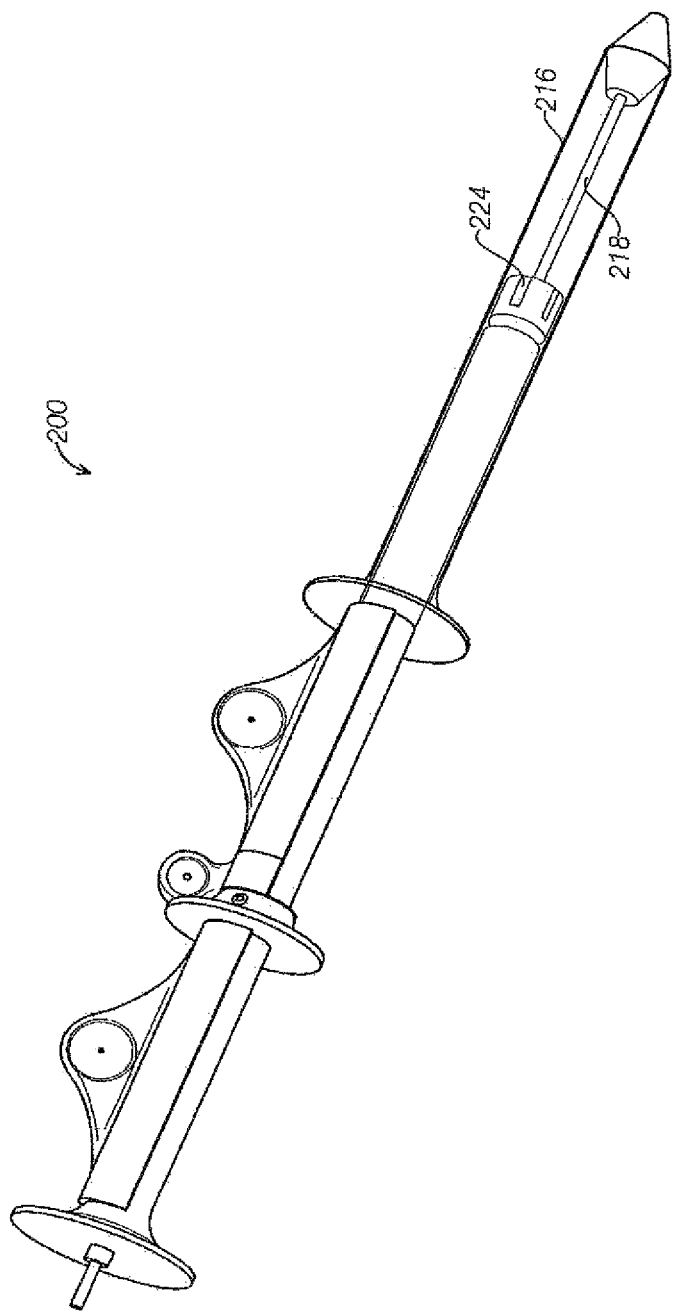
FIG. 2A shows another embodiment of a prosthetic delivery device.
Figure 2B:
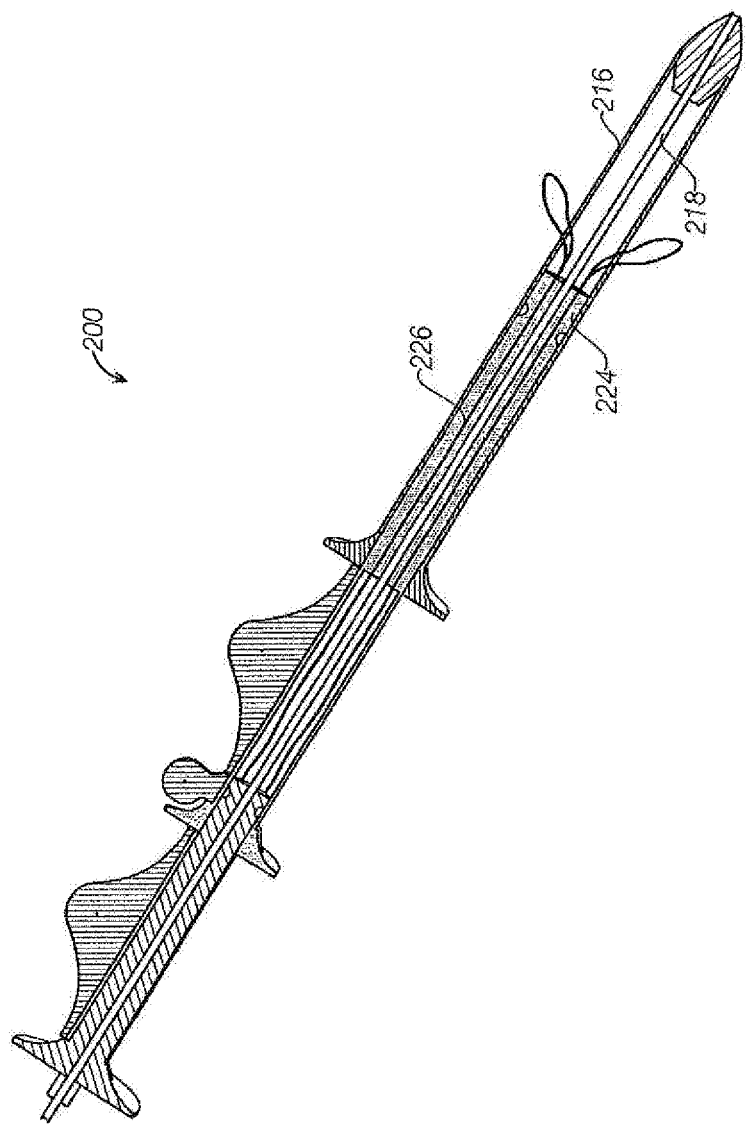
FIG. 2B is a cross-section of FIG. 2A.

FIGS. 2A-2B show a delivery device 200 that is configured to control the expansion of the proximal portion of the anchor (as is the embodiment in FIG. 1) while allowing for recapture and/or movement of the proximal anchor was deployed. The delivery device 200 thus includes a central stem 218, a proximally retractable sheath 216, and a central control assembly. The central control assembly includes a plurality of looped tethers 226 (see FIG. 2B) extending therethrough and an annular member with constraining elements 224 extending therearound.

The tethers 226 extend down the center of the device 100. The tethers 226 form a loop at the distal end through which the constraining elements 224 extend. In use, the looped tethers 226 can be extended through portions of a prosthetic valve, such as the proximal anchor, and then the ends of the tethers 226 can loop around the constraining elements 224 (which are held in place by the sheath 216, as described below). The tethers 226 can be configured to be loosened using controls in the handle. When the loops of the tether 226 are loosed, the proximal end, of the prosthetic valve can expand, and when the loops are tightened, the proximal end of the prosthetic valve can collapse. Exemplary materials for the tethers 226 include polymers such as Force Fiber HDPE tether, a wire of nitinol, tungsten or stainless steel, or a braided tungsten or stainless steel cable.

The constraining elements 224 can be formed, for example, of a shape memory material and are configured to extend through the loops of tether 226, as described above. In some embodiments, the constraining elements 224 include a plurality of shape memory, e.g., nitinol, flaps or strips that are held down by the sheath 216, but open, release, or expand when the sheath 216 is retracted. The sheath 216 can thus retain the plurality of constraining elements 224 in closed or captured configurations, thereby ensuring that the tethers remain looped through the valve.

FIGS. 2A and 2B show the sheath 216 extended fully distally over the stem 218. In this configuration, the valve prosthesis would be fully enclosed within the sheath 216— with the distal portion of the valve prosthesis held in the collapsed configuration by the sheath 216 and with the proximal portion of the valve prosthesis held in the collapsed configuration by the tightened tethers 226, which are in turn held in place by the constraints 224.

Figure 3:
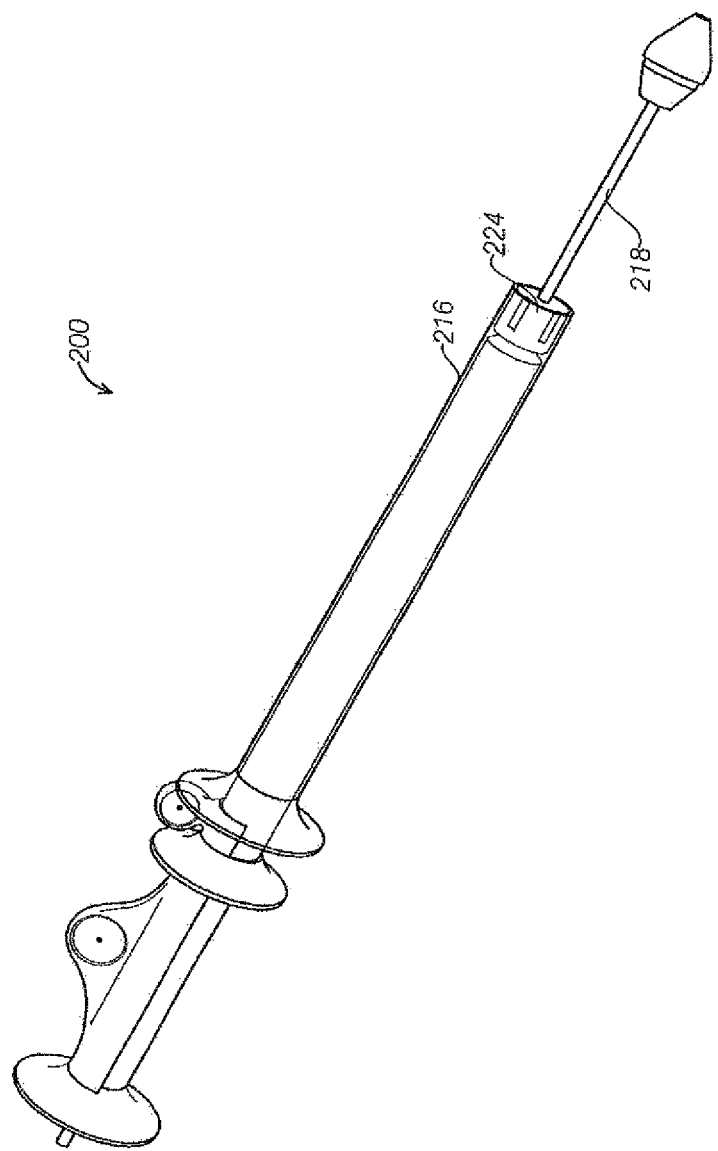
FIG. 3 shows the delivery device of FIG. 2A with the sheath partially proximally withdrawn.

FIGS. 2A-6 illustrate a sequence of using the device 200. Thus, FIG. 3 shows the delivery device 200 after sheath 216 has been partially proximally withdrawn relative to the central stem 218 such that the distal end of the sheath 216 is substantially aligned with the distal end of the annular member with constraining elements 224. In this position, the distal end of the prosthesis, e.g., the distal anchor, would be allowed to self-expand and/or deploy. However, because the distal end of the sheath 216 is still distal to the capture elements 224, the capture elements 224 are still in their closed configuration, thereby maintaining their hold on the tethers 226.

Figure 4:
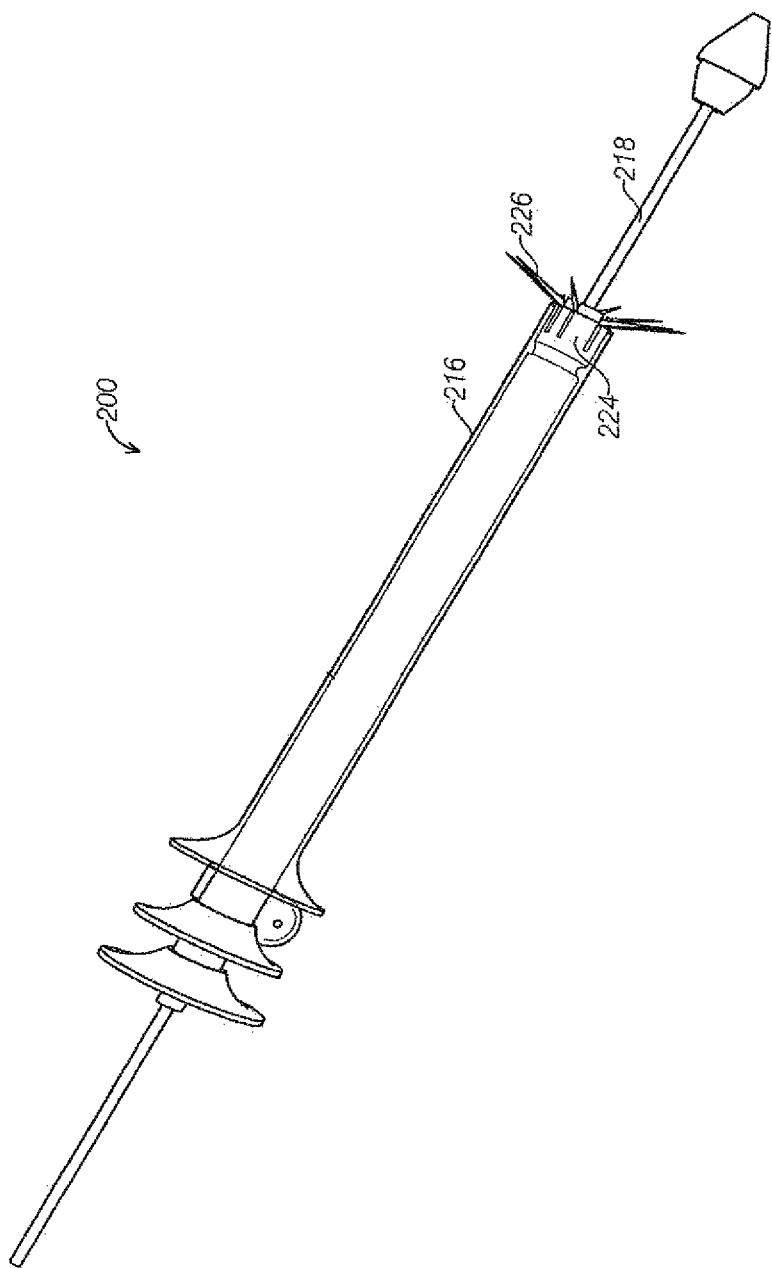
FIG. 4 shows the delivery device of FIG. 2A with the tethers exposed.

FIG. 4 shows the delivery device after tethers 226 are distally advanced by distally advancing the proximal most handle 109. Distally advancing the looped tethers 226 loosens the loops relative to the prosthesis and allows the proximal portion of the prosthesis to be expanded. Tethers 226, however, are still in position relative the proximal side to be able to collapse the proximal anchor if needed.

Figure 5:
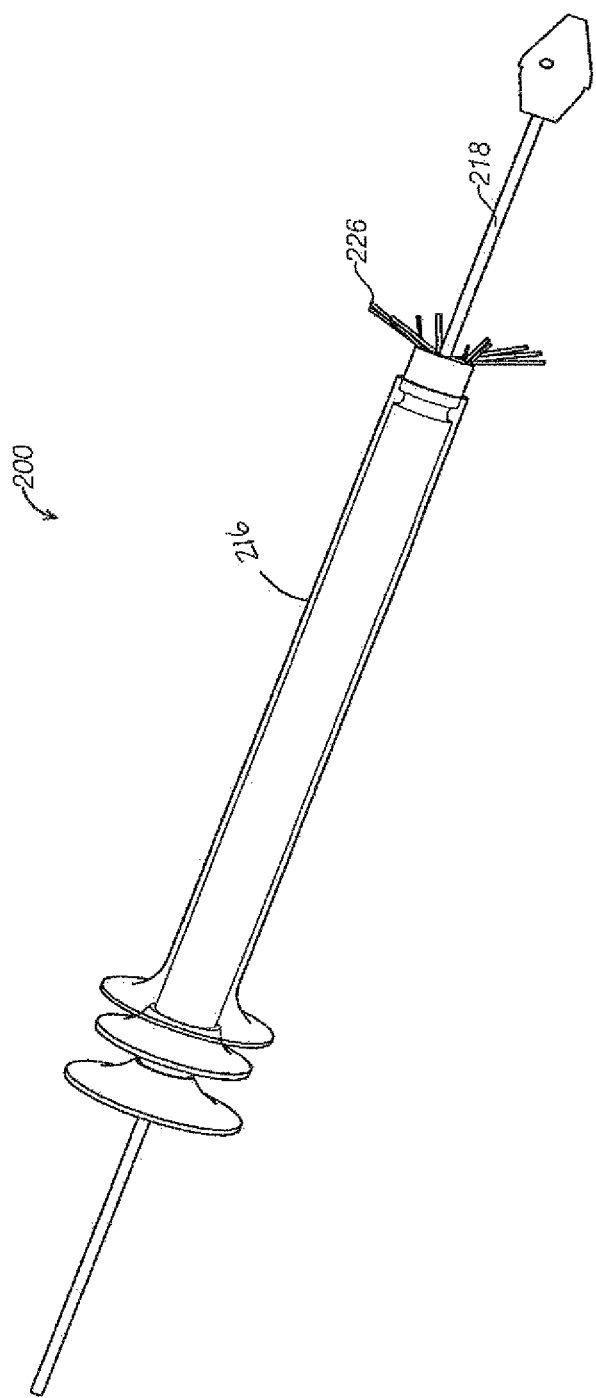
FIG. 5 shows the delivery device of FIG. 2A with the tethers partially retracted.

Thus, referring to FIG. 5, the tethers 226 can advantageously be pulled distally to tighten the tethers and collapsing the proximal anchor (e.g. for movement and/or optimal placement of the prosthesis). FIG. 5 thus shows the tethers 226 tightened, which would in turn recollapse the proximal portion of the prosthesis. If needed, the entire valve can be retrieved back inside sheath 216, where the delivery device looks like what is shown in FIG. 2 after sheath has been advanced distally.

Figure 6:
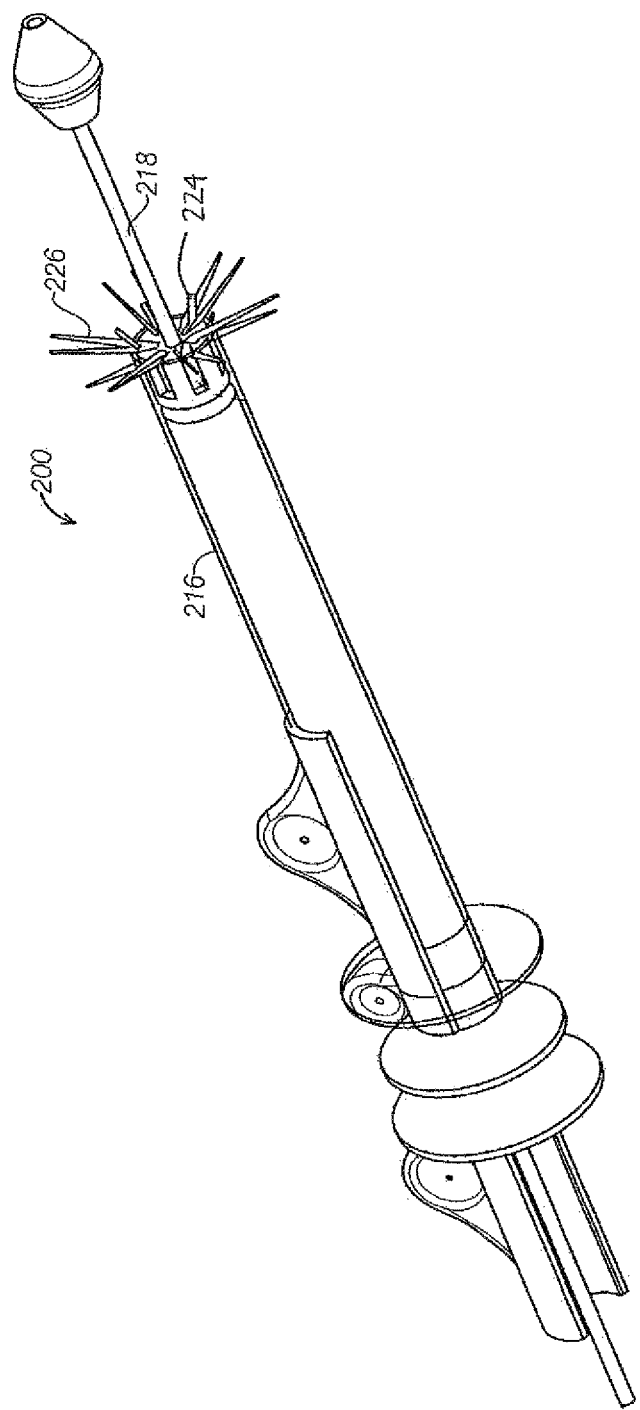
FIG. 6 shows the delivery device of FIG. 2A with the tethers and retaining elements fully released.

Referring to FIG. 6, to fully deploy and release the prosthesis (i.e., after positioned properly with the tethers 226 still attached), the sheath 216 can be pulled distally past the constraining members 224, thereby causing the tethers 226 to pop out of the constraining members 224.

Figure 7:
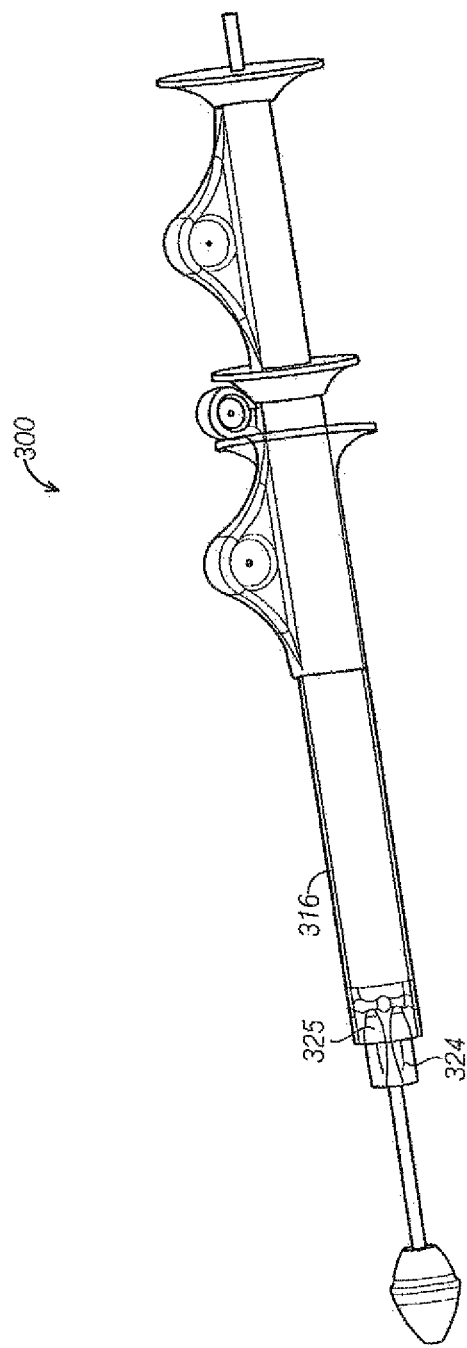
FIG. 7 shows another embodiment of a prosthetic valve delivery device.

FIG. 7 is another embodiment of a delivery device 300 that is similar to the embodiment in FIGS. 2-6. In this embodiment, however, capture elements 324 do not have shape memory configurations. In this embodiment, capture elements 324 are configured to passively change configurations from a closed or capture configuration to an open or release configuration. Each of the retaining elements 324 is configured to mate with, or by keyed with, an indentation 325 of the central assembly. In this embodiment, the capture elements 324 have a substantially triangular shape. The mating configurations (with the sheath 316 thereover) keeps the capture elements 324 mated with the indentations 325. When sheath 316 is retracted past the capture elements 324, the capture elements 324 will not automatically revert to an open configuration due to the material properties of the retaining elements 324. Rather, they will be forced to an open configuration due to the self-expanding properties of the proximal portion of the prosthesis. Tethers, or other additional restraining elements can again be used to further control the expansion of the proximal portion of the prosthesis, as is described in the embodiment of FIGS. 2-6.

Figure 8:
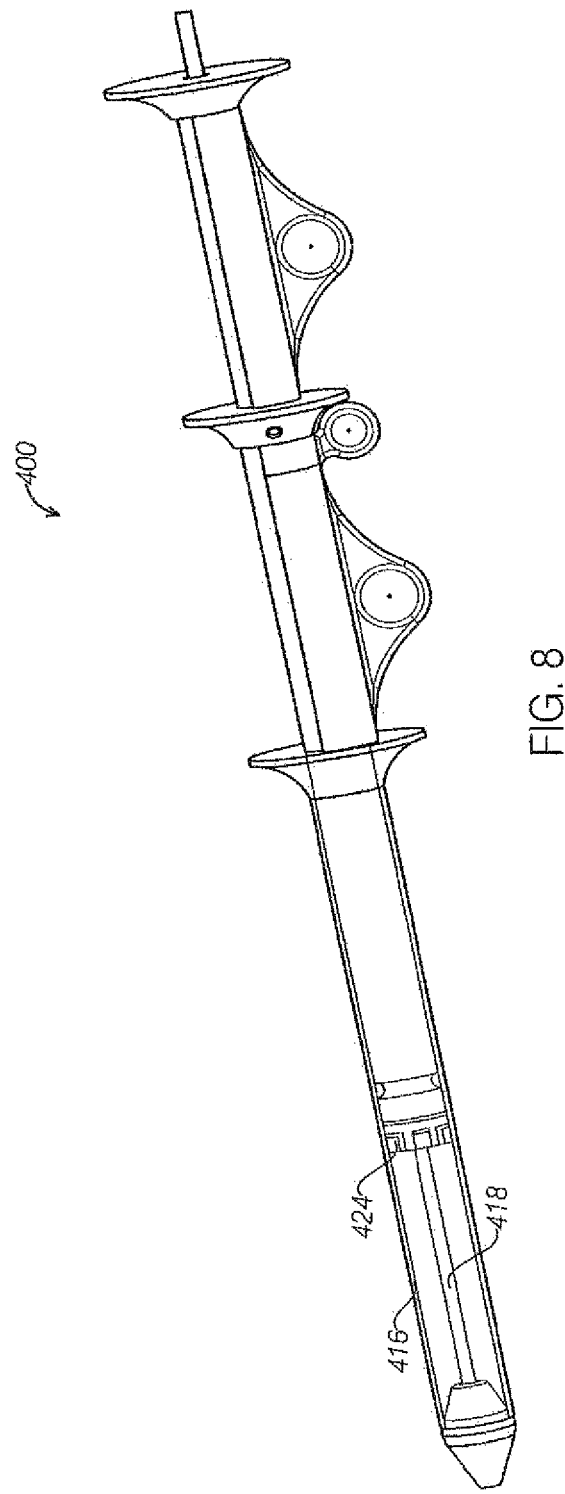
FIG. 8 shows another embodiment of a prosthetic valve delivery device.

FIG. 8 illustrates another delivery device 400. The delivery device 400 includes a central stem 418 and a sheath 416, similar to as described with respect to other devices described herein. Further, capture elements 424 function similar to capture elements 324.

Figure 9:
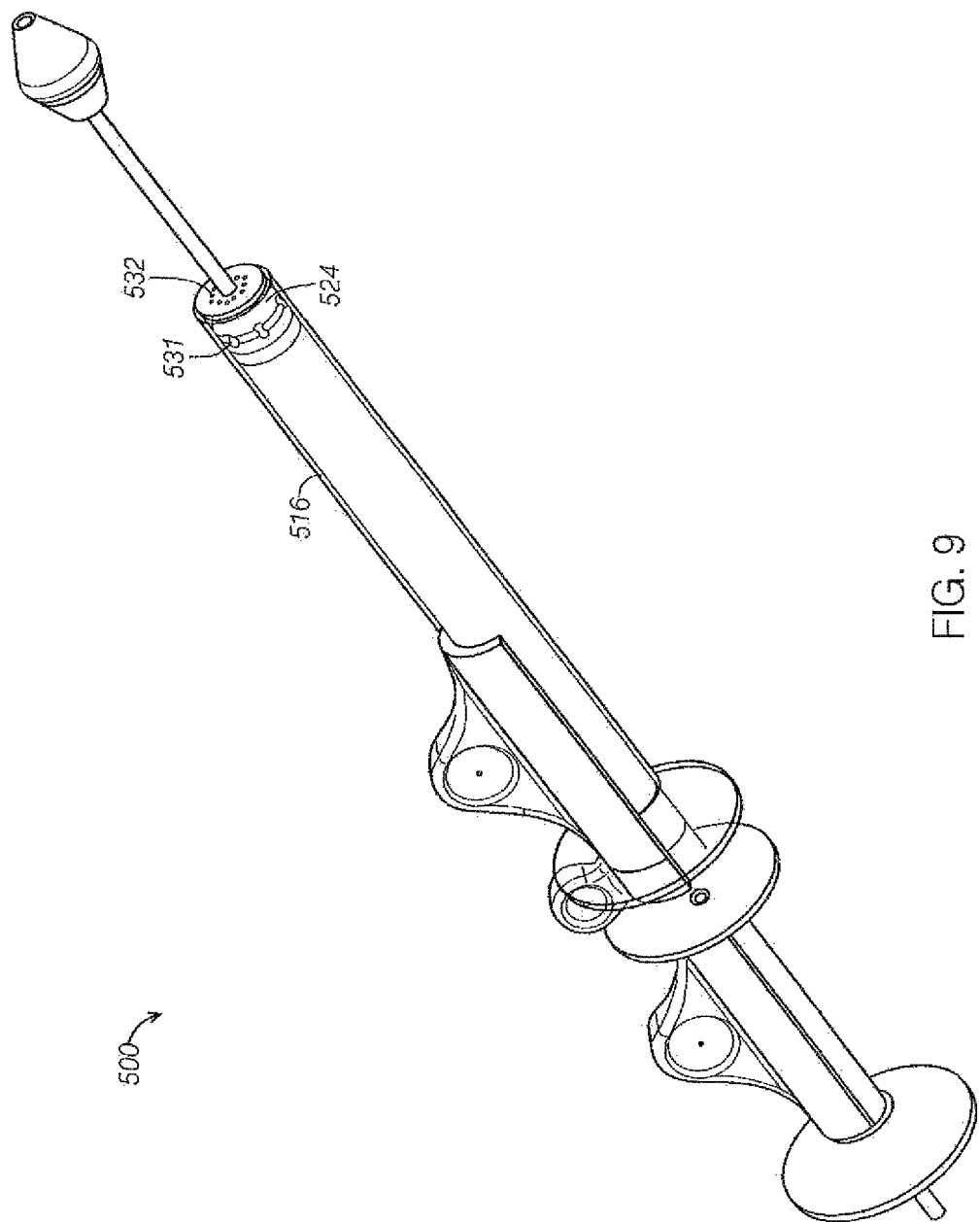
FIG. 9 shows another embodiment of a prosthetic valve delivery device.

FIG. 9 illustrates an alternative delivery device 500 having a tether ends retainer 524 with pockets 531 therein configured to hold the ends of a tether (i.e., rather than having the tether loop around a capture element). The details of such a tether ends retainer 524 be described further below with respect, for example, to FIG. 11A. The tethers extend through tether lumens 532. In some embodiments, the ends of the tethers (or sutures, wires, or other controllable restraining elements) can include a radiopaque marker in a region configured to change position when the proximal portion has been released from the restraining elements. For example, the radiopaque marker can be in a region that is configured to "open." By including a marker on the portion that is configured to change position when the proximal portion has been released (and optional expanded), visualization can be used to determine when the proximal portion has been released by the restraining elements and expanded.

Figure 11A:
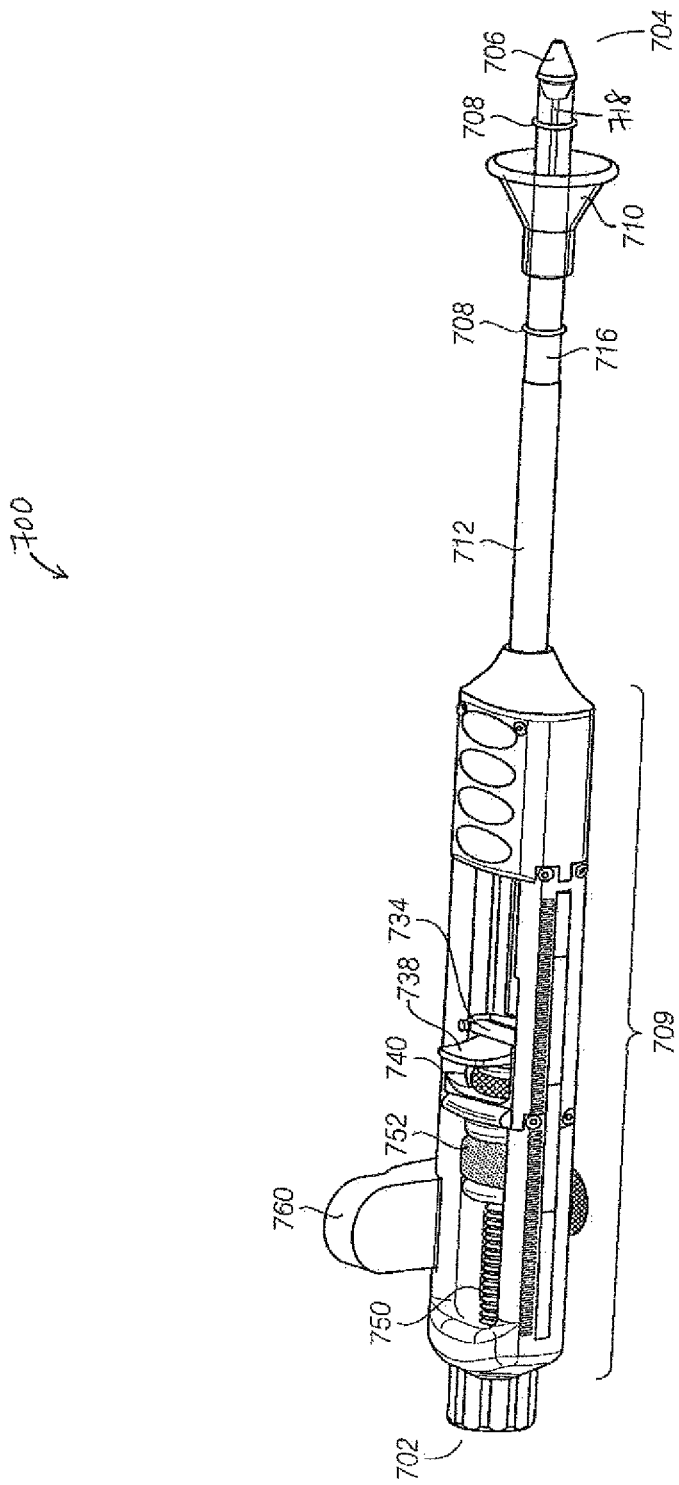
FIG. 11A shows another embodiment of a prosthetic valve delivery device.
Figure 11B:
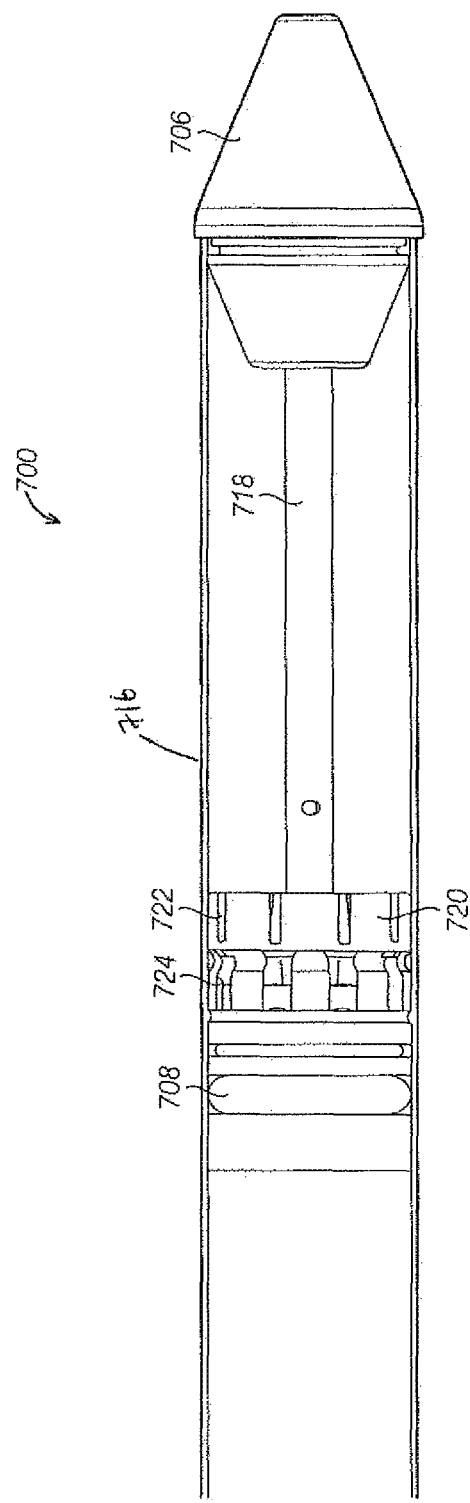
FIG. 11B shows a close-up of the delivery device of FIG. 11A without an outer sleeve and a tether loading cone.
Figure 11C:
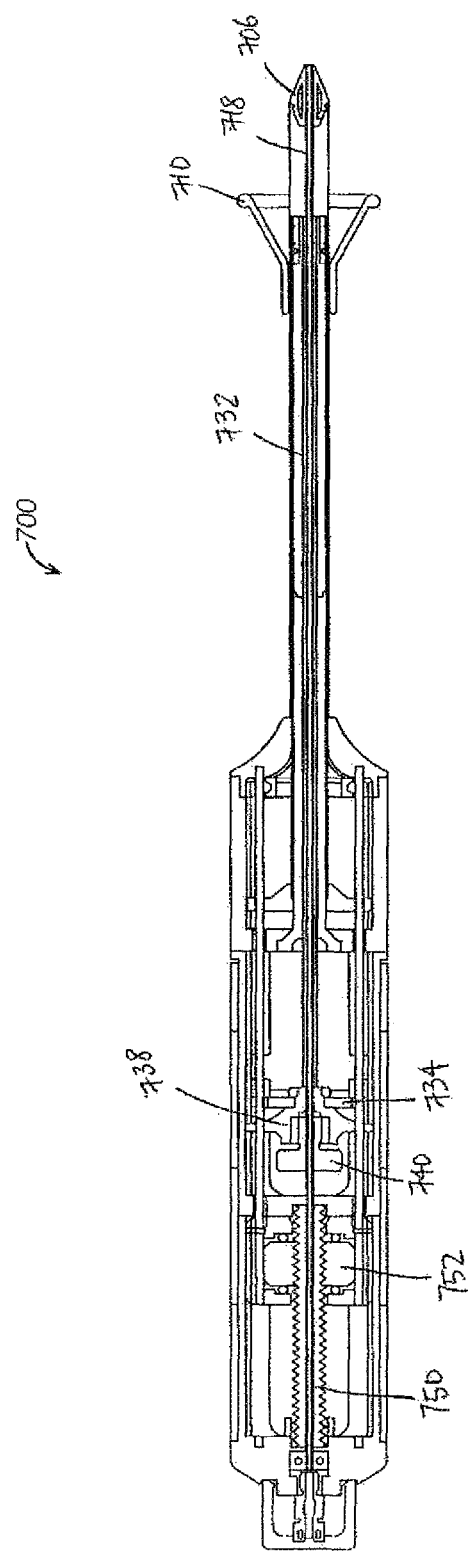
FIG. 11C shows a cross-section of the delivery device of FIG. 11A along its longitudinal axis without a grasper.

FIG. 11A shows another embodiment of a prosthetic valve replacement delivery device 700. The delivery device 700 includes a device proximal end 702 and a device distal end 704. As can be seen from FIG. 11A through 11C, the delivery device 700 has an elongated portion that terminates at a nosecone 706 at the device distal end 704. The nosecone 706 is coupled to a central stem 718, which is in turn coupled to a tether ends retainer 720 (described in detail below). The elongated portion includes an outer sheath 712 and an inner sheath 716. The central stem 718 also couples to a series of tether/suture maintaining hypodermic tubes that are able to slide along the central stem 718 (the hypodermic tubes will be further described below). The inner sheath 716 is configured to slide relative to the central stem 718 (extend and retract) to cover or expose certain retaining features of the delivery device, e.g., the tether ends retainer 720, (see FIG. 11B) as well as aid with maintaining the prosthetic valve within the delivery device 700 prior to deployment. The device proximal end 702 includes a handle 709 for holding onto the delivery device. Other components maintained within the proximal portion of the delivery device 700 will be discussed below. FIG. 11B shows a close-up of the distal end the delivery device 700, where it is more apparent that the nosecone 706 is attached to the central stem 718 and the central stem 718 is coupled to a tether ends retainer 720. FIG. 11C shows a cross-sectional view of the delivery device 700.

As best shown in FIG. 11B, the nosecone 706 is located at the device distal end 704 of the delivery device 700 and includes a tapered distal tip. The nosecone 706 is configured to aid with inserting the delivery device 700 into a position within a patient's heart for successful valve placement. The nosecone 706 tip has a small surface area such that if the nosecone 706 touches any portion of the patient's heart, less damage will be done to the heart. The nosecone 706 tip is also rounded or blunt so as to decrease the risk of puncturing the patient's heart if the nosecone tip contacts the surface of the heart.

Tethers 726 (see FIG. 20) aid with maintaining the prosthetic valve within the device 700. In most cases, the tethers are made of suture materials. The proximal ends are maintained by the tether control lever 738 while the distal ends are maintained within the tether retainer 720. The lengths of tether extend along and around the center stem 718, and each thread through a separate tubular structure. The tether ends that couple to the tether retainer 720 further include a feature for coupling the tether ends to the tether retainer 720, as is further discussed below.

Figure 16A:
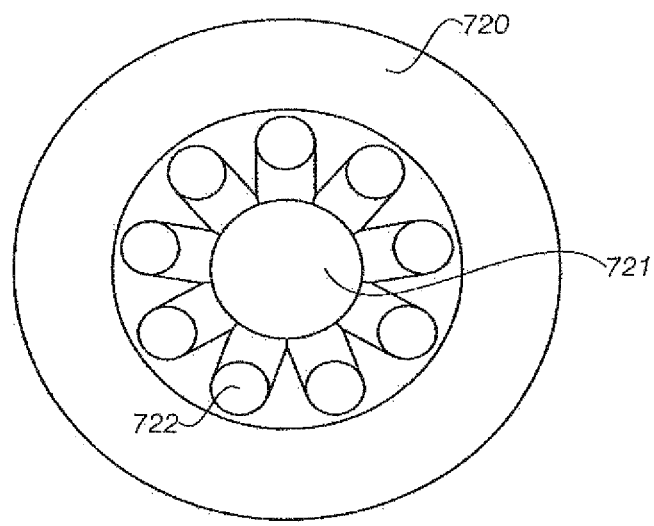
FIG. 16A and FIG. 16B show a tether ends retainer from on top and angled side view.
Figure 16B:
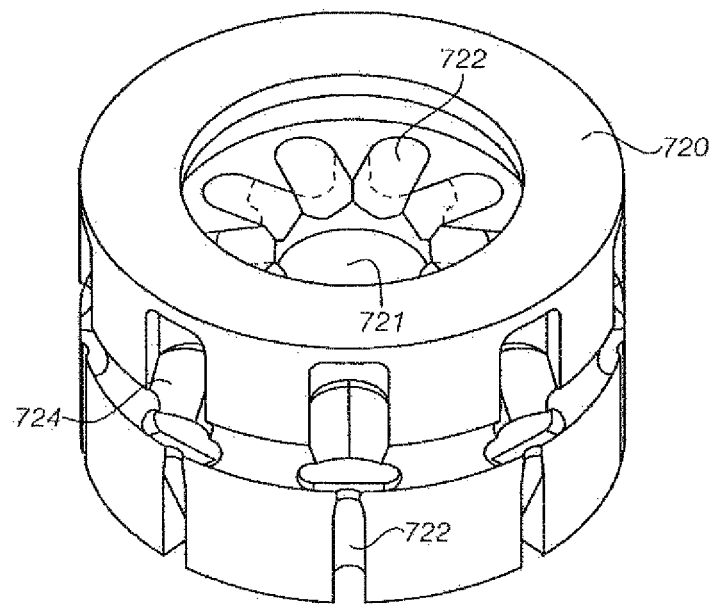

The distal ends of the tethers are configured to loop through the proximal end, such as the prosthetic anchor, of the prosthetic valve. The distal ends of the tethers, once looped through the prosthetic anchor, are maintained by the tether retainer 720. The tether retainer 720 in relation to the delivery device 700, to the central stem 718 and the nosecone 706, can be seen in FIG. 11B. FIG. 16 also shows the tether retainer 720 unattached and by itself from two different angles. The tether retainer 720 has a substantially annular or cylindrical shape and has dimensions that allow it to fit within the inner sheath 716. The tether retainer 720 includes a tether retainer center aperture 721 and an array of apertures 723 within its internal core. The tether retainer center aperture 721 maintains the tether retainer 720 within the delivery device 700. The tethers threaded through the array of apertures 723, one tether per aperture. A series of hypotubes 732 (see FIG. 13C) are aligned with each of the apertures 723. Each single tether is threaded through a hypotube 732 prior to exiting through the array of apertures. The hypotubes 732 allows the individual tethers to be evenly spaced about the delivery device 700 and prevents asymmetric arrangement of the tethers around the central stem 718. Symmetric loading ensures symmetric tensioning of the proximal end petals of the prosthetic valve, improving the loading of the device and the release characteristics. In this embodiment, there are nine apertures and nine hypotubes that maintain individual tethers at an even spacing within the delivery device body. In other examples, there may be more or fewer apertures and hypotubes for maintaining individual or multiple tether lines.

Figure 20A:
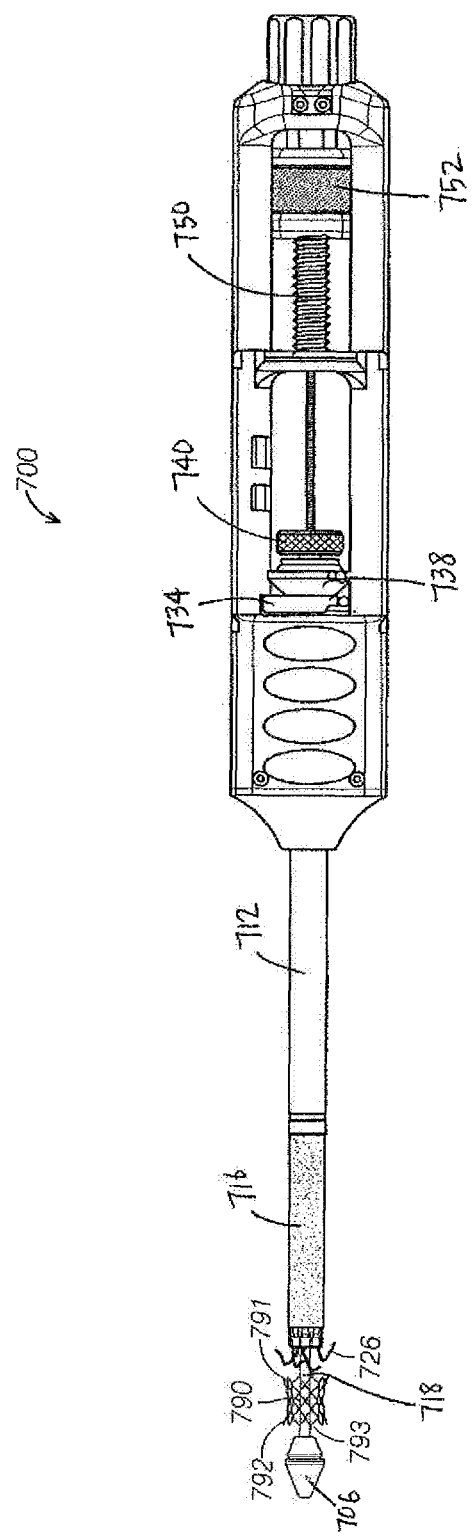
FIG. 20A shows the delivery device of FIG. 11A having a prosthetic valve inserted onto the distal end but uncoupled to the delivery device.
Figure 20B:
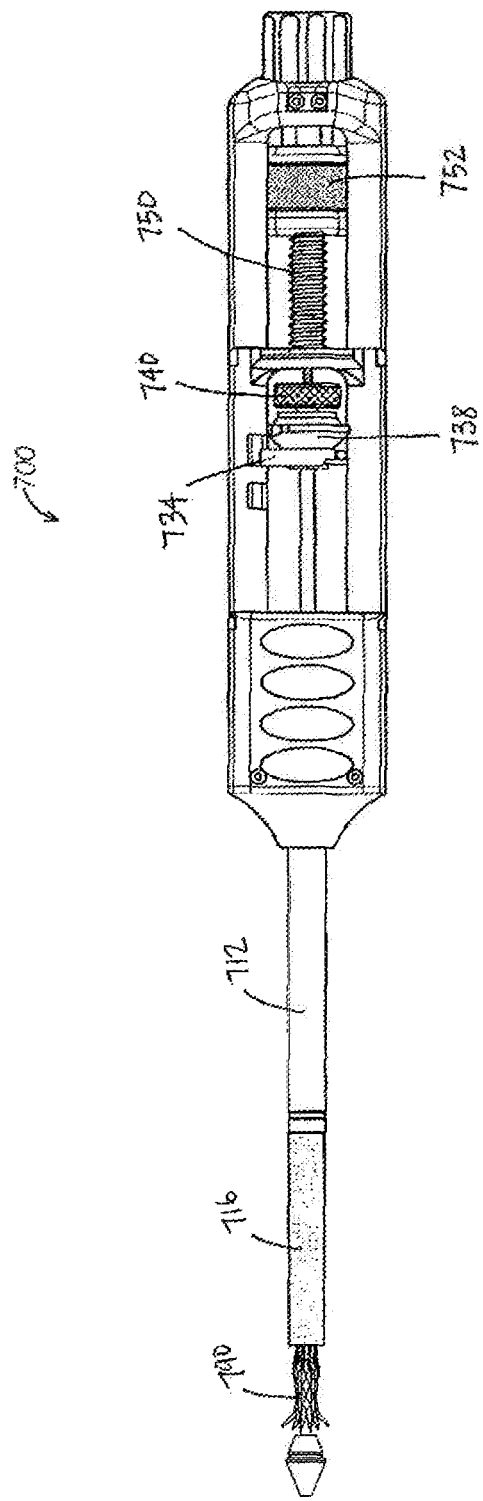
FIG. 20B shows the delivery device of FIG. 11A having the prosthetic valve attached at its proximal end but not drawn into the delivery device.

Once all the tethers have been looped around the proximal end petals of the prosthetic valve, the free tether ends are brought back to the tether retainer 720. As can be seen from FIG. 16B, the outer surface of the tether retainer 720 includes a series of evenly spaced tether pockets 724 that are in fluid connection with corresponding series of tether slots 722. FIG. 20A shows the delivery device 700 having free tether 726 ends. Each tether 726 distal end can include a truncated cone, where an infinity knot at each tether end maintains the tether within the corresponding truncated cone. The truncated cones can be tapered distally to proximally. Each truncated cone may be inserted into one of the pockets 724 and then each tether maintained within the corresponding slot 722. The inner sheath 716 may be extended distally to cover the tether pockets 724. This aids with keeping the tether ends within the tether pockets 724.

The truncated cones on the distal end of the tethers may be made of any suitable rigid materials. The truncated cones are designed such that they easily release from the tether retainer 720. The geometry of the truncated cone are configured specifically to fit the tether pockets 724. The tether pockets 724 may also include additional features for maintaining the truncated cones of the tether ends when under tension. Further, the feature in the distal ends of the tethers need not be conical, but can be spherical or otherwise have a different shape. Materials for the distal features may include plastics, stainless steel, non-reactive polymers and so forth. In one example, the distal features are fabricated at least partially from tantalum.

The tether retainer 720 may also have a groove at its proximal end for an O-ring 708. The O-ring is to prevent excessive blood from penetrating rest of the delivery device during a procedure. Moreover, the distal end of the tether retainer 720 may have a diameter slightly less than that of the proximal end. This allows the tether retainer 720 when fitted with the O-ring to still fit within the inner sheath 716.

The tethers 726 are used to control the prosthetic valve within the delivery device and aid with placement of the prosthetic valve at the mitral valve site. The series of distal tether ends are maintained within the tether retainer 720. Referring to FIG. 11A, the series of proximal end tethers are held by tether (atrial) control lever 738. The tether control lever 738 includes a series of apertures 739 for holding the proximal tether ends, where appropriate knots at the proximal tether ends hold the tethers in place. Alternatively, proximal tether ends may include a knot holding feature that prevents the tether end from slipping through the tether control lever 738. The tether control lever 738 is a lever that allows the operator to easily adjust the tension on the tether ends with their thumb. Once the tether ends have been threaded through the proximal end petals of the prosthetic valve and slotted into the tether pockets 724, the operator may tension the tether by pulling back on the tether control lever 738 and pull the prosthetic valve into the inner sheath 716. After the tether ends have been loaded, the tether control lock 734 may be flipped down to contact a tether control notch 736. The tether control lock 734 maintains the tethers in place.

Figure 17:
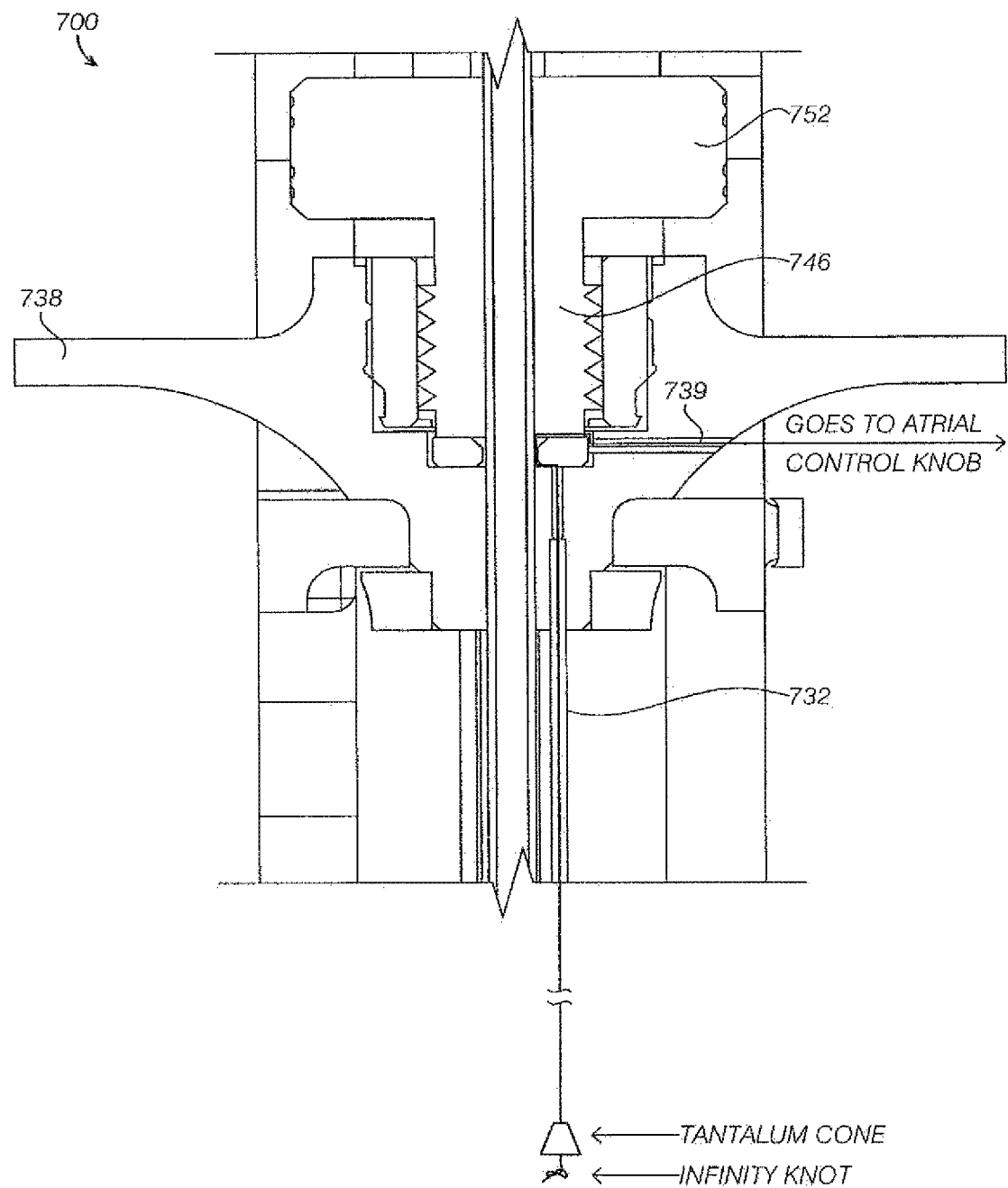
FIG. 17 shows a cross-section of a tether control lever and a secondary release knob.

Once the replacement have has been loaded into the delivery device 700, tension is maintained on the tethers until the prosthetic valve has been properly positioned. The mechanism for maintaining tension on the tethers includes the thumb screw 752 and the tether control lever 738. FIG. 17 is a close-up of a cross section showing the secondary release knob 7140 and the tether control lever 738. A few of the hypotubes 732 are visible. The proximal tether ends enter the tether control lever 738 through tether control channels 739, and jog around a washer that is adjacent to secondary release knob 140 before it enters the hypotube 732 jogs. A knot at the end of the proximal tether end prevents this end from slipping through the tether control lever 738. The secondary release knob 740 when it is tightened against the washer adjacent to the tether control lever 738 maintains tension on the proximal tether ends when the tether control lever 738 is pulled proximally.

Figure 12A:
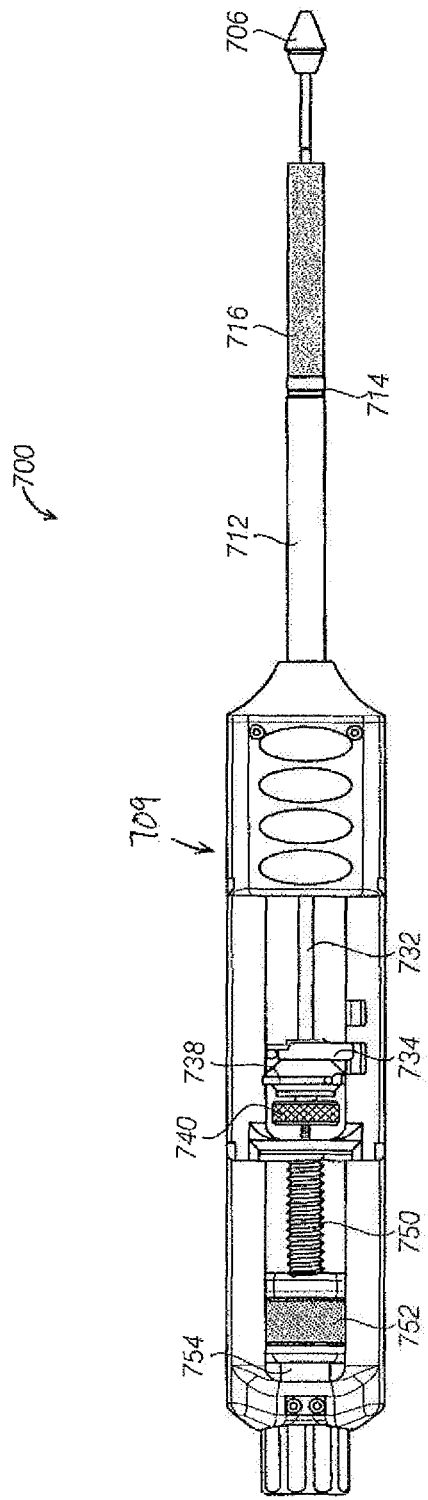
FIG. 12A shows the delivery device of FIG. 11A unsheathed.
Figure 12B:
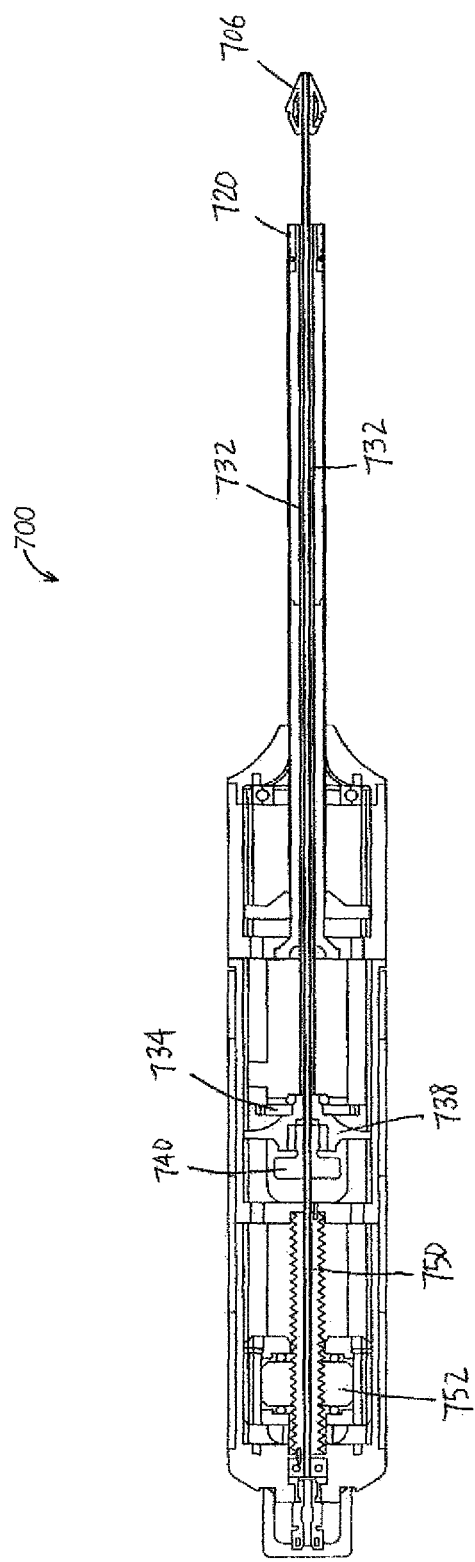
FIG. 12B shows a cross-sectional view of the unsheathed delivery device of FIG. 12A.
Figure 12C:
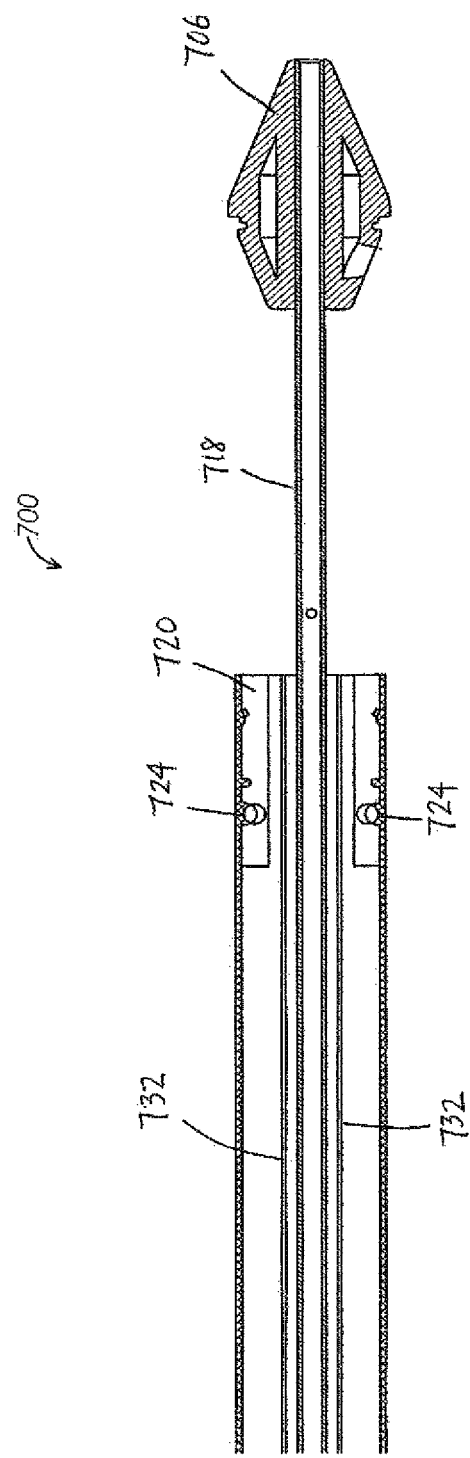
FIG. 12C shows a close up of the cross-section of the distal end of the unsheathed device of FIG. 12A.

Referring to FIGS. 12A-12C, the handle 709 of the delivery device 700 includes the tether control lever 738. The tether control lever 738 is coupled with a secondary tether release knob 740. The tether control lever 738 and the secondary tether release knob 740 work to maintain the second (proximal) ends of the tethers. Also coupled to the tether control lever 738 on its distal side are the series of hypodermic tubes 732 (hypotubes for short) that are disposed around the central stem 718. The series of hypotubes 732 each hold one tether and are able to extend and retract along with the tether control lever 738.

Figure 13A:
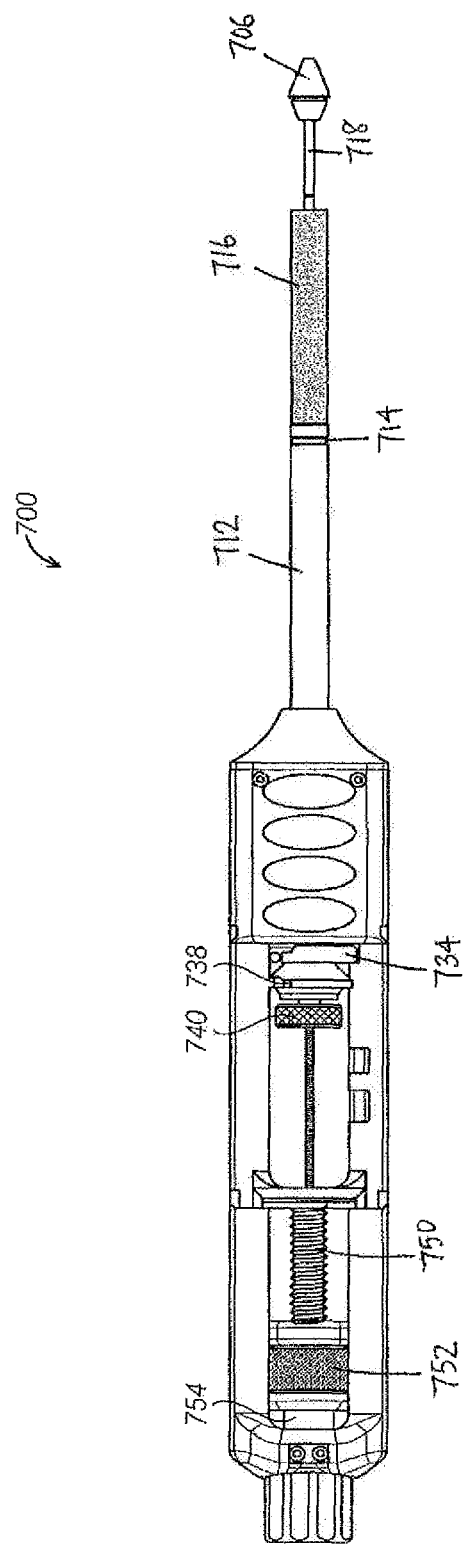
FIG. 13A shows the fully unsheathed delivery device of FIG. 12A where a tether control knob has been pushed distally along with a series of hypotubes for deploying a proximal end of a replacement prosthetic valve.
Figure 13B:
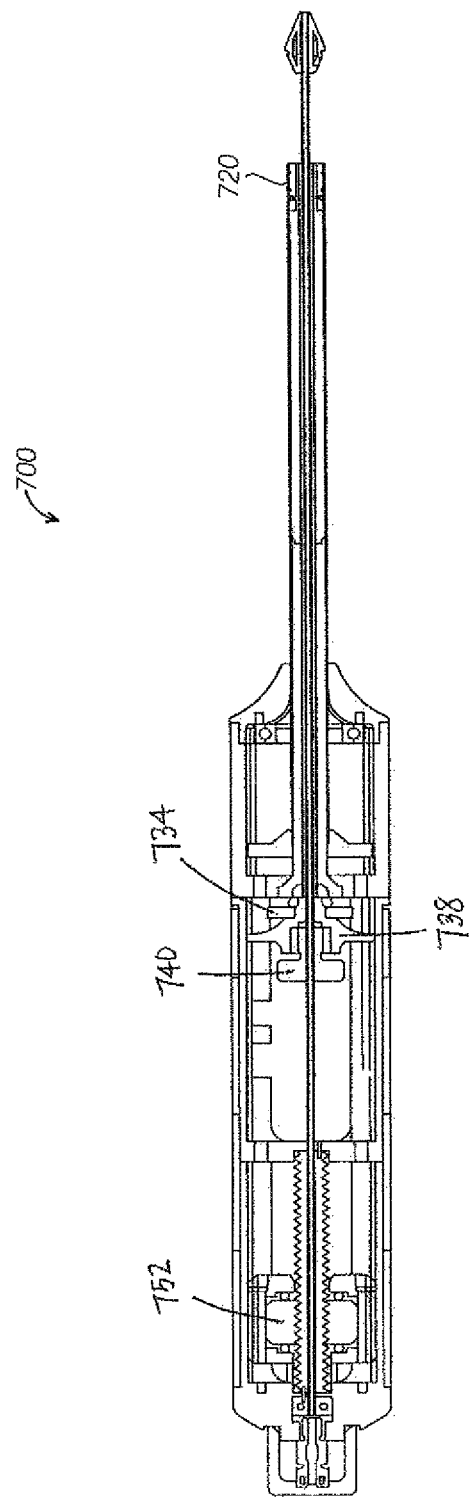
FIG. 13B is a cross-sectional view of the fully unsheathed delivery device of FIG. 13A.
Figure 13C:
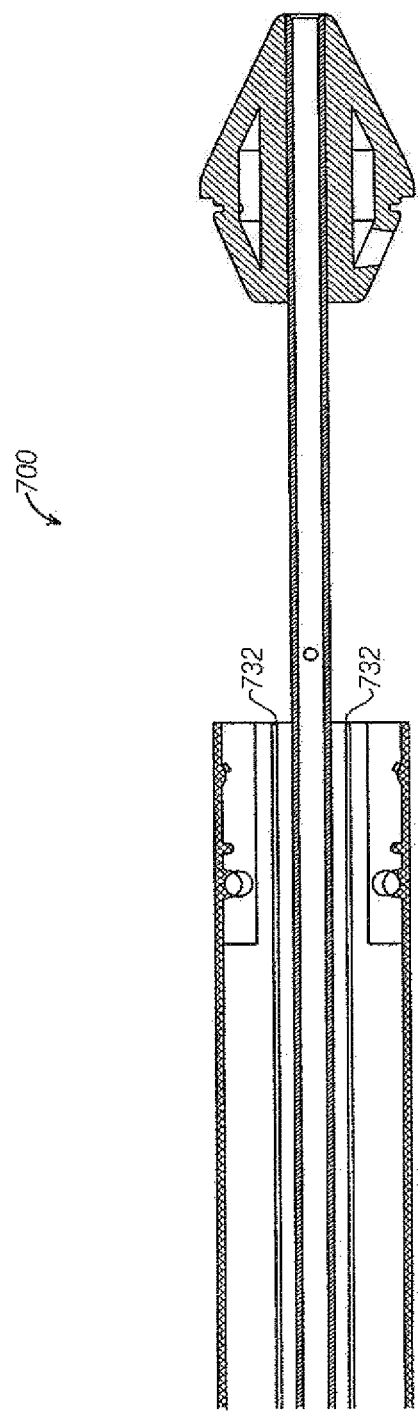
FIG. 13C shows a close up of the cross-section of the distal end of the unsheathed device of FIG. 13A where a series of hypotubes have advanced distally.

FIGS. 13A-13C show the delivery device 700 where the tether control lever 738 and secondary tether release knob 740 have been pushed distally. This distal movement moves the series of hypotubes 732 as well from a more proximal location to a more distal location along the central stem 718 such that the series of hypotubes 732 meet and abut the tether ends retainer 720. When doing so, the tether ends retainer 720 remains stationary in its position on the central stem 718. The hypotubes 732 aide with keeping the tethers separated when there is slack in the tether lines as they are moved forward during deployment or when the prosthetic valve is being loaded. Notes that the tether ends retainer 720 remains stationary in its position on the central stem 718. This places the prosthetic valve in an optimal location on the delivery device 700 for loading and deployment.

Referring to FIG. 12A The handle portion 709 also includes an inner sheath control knob 752 which is coupled to a lead screw 750. These two components work to extend or retract the inner sheath 716. Sitting on the proximal side of the sheath control knob 752 is a clip 754 that prevents the inner sheath 716 from retracting too proximally until the prosthetic valve is ready to fully deploy, at which time the clip 754 may be pulled off.

In use, a prosthetic valve is first loaded into the device 700. FIG. 20A shows the loading of an exemplary mitral valve prosthesis 790. The prosthesis valve 790 generally has a cage-like appearance with a center aperture 793. The prosthetic valve 790 includes a proximal end petals 791 and distal end petals 792. In this embodiment, the mitral valve prosthesis includes two anchors having a series of cells with radially extending petals or loops. To load the prosthetic valve into the delivery device 700, the central stem 718 and nosecone 706 are first inserted through the center aperture 793 of the prosthetic valve. Next, individual lengths of tether 76 from a series of tethers originating from the device proximal end 702 and disposed around the central stem 718 portion, loop around each petal portion from the proximal end of the prosthetic valve (the end closer to the proximal end of the delivery device). While not all of the petals from the proximal end of the prosthetic valve need to be coupled to an individual tether, enough petals should be coupled to individual tethers such that when the series of tethers are pulled axially in the proximal direction, all the petals of the proximal end of the prosthetic valve will uncurl equally and evenly, and close in around the central stem 718. Then the free ends of the tether 726 having the truncated cones may be slipped into corresponding pockets 724 of the tether retainer 720.

After tensioning the tethers/sutures and pulling the proximal side petals of the prosthetic valve straight using the tether control lever 738, the inner sheath 716 may be extended distally with the sheath control knob 752 such that it begins to cover the straightened out proximal side petals of the prosthetic valve. Further retracting the tether retainer 720 will cause the tensioning forces to translate to other parts of the prosthetic valve. This additional tension is now able to pull the distal side petals on the prosthetic valve towards the inner sheath 716. Recall that, at this point, the proximal end petals are already maintained within the inner sheath 716, so that further tension on the proximal end of the prosthetic valve will now straighten out the distal petals of the prosthetic valve. Once the distal end petals of the prosthetic valve are completely retained within the inner sheath 716, then the delivery device 700 is fully loaded. The inner sheath 716 may be extended fully distally until it meets with nosecone 706. This can be done by rotating a sheath control knob 752. Rotating the sheath control knob 752 in one direction will extend the inner sheath 716 until it meets up with the nosecone 706, while rotating the sheath control knob 752 in the opposite direction will retract the inner sheath 716 proximally along the elongated portion 701 of the delivery device 700.

Figure 20C:
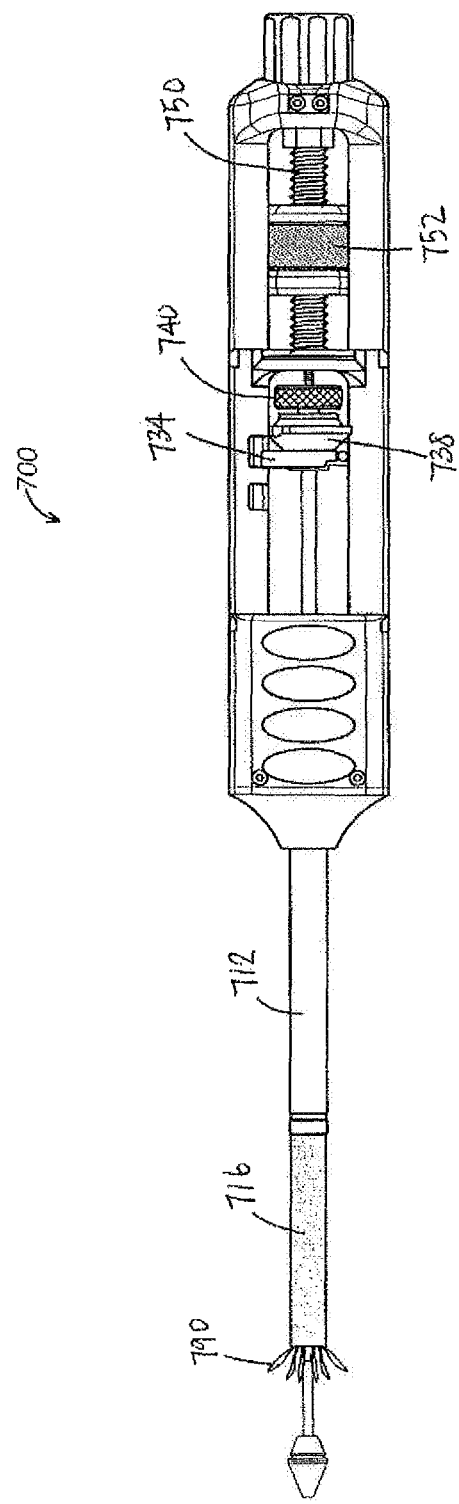
FIG. 20C shows the delivery device of FIG. 11A having the prosthetic valve partially drawn into the delivery device.

In some embodiments, a tether loading cone 710 (see FIG. 11A) may be used to aid with loading a prosthetic valve into the delivery device 700. The operator can apply tension to the series of tethers using the tether control lever 738 such that the prosthetic valve proximal petals are straightened enough to fit into the inner sheath 716. The tether loading cone 710 aids with directing the individual petals into inner sheath 716. As the operator continues to pull the series of tethers proximally, the proximal end petals will be completely housed within the inner sheath 716 followed by the central portion of the prosthetic valve (FIG. 20C). Once the prosthetic valve central portion has been pulled into the inner sheath 716, the tension being exerted on the prosthetic valve will continue to pull the prosthetic valve axially in the proximal direction such that the distal end petals now begin to uncurl and straighten out while being pulled into the inner sheath 716. The prosthetic valve is now completely loaded when the entire valve is maintained within the inner sheath 716 even though tension is still being maintained on the proximal end of the prosthetic valve through the tether control lever 738. Once the prosthetic valve has been loaded, the tether loading cone 710 may be removed and the valve placement procedure may proceed.

An outer sheath may be used to assist with delivery of the device 700. Thus, the delivery device 700 includes an outer sheath 712, which can be seen in FIGS. 12A-12C. FIG. 12A is a schematic of the delivery device 700. FIG. 12B shows a cross-section of the delivery device 700 along a longitudinal plane and FIG. 12C shows a close-up of the cross-section for the distal end of the delivery device 700. FIG. 12A shows the outer sheath 712 relative to the inner sheath 716. The outer sheath 712 is primarily used during insertion of the delivery device 700 into a patient's body cavity. The outer sheath 712 is slide-able along the elongated portion 701 to cover the elongated portion 701 up to the nosecone 706. Once an incision is made, a suture is purse string stitched around the perimeter of the incision. This allows the incision to be made smaller by pulling on the (purse string stitched) suture. As can be seen from FIG. 12A, the outer sheath 712 includes an outer sheath groove 714 disposed around its distal end. The incision may be cinched down around the outer sheath groove 714 such that the incision site is essentially closed off except for the delivery device 700. This is advantageous because it minimizes exposing a patient's internal system to the outside environment thereby reducing risk of harmful agents coming into contact with a patient's internal system. In addition, having the incision site cinched around the delivery device 100 also reduced the amount of blood loss during the procedure.

Because the outer sheath 712 is configured to move axially with respect to the remainder of the delivery device 700, an operator will still be able to maneuver the delivery device 700 within the incision site axially and also to some extent in a circular fashion within the incision site for finding optimal position to deploy the prosthetic valve. Thus the outer sheath 712 remains stationary once the incision site sutures have been tightened around the outer sheath groove 714, and the delivery device 700 is able to deliver the prosthetic valve with use components of the delivery device that are further described below.

Using the sheath 712, the operator may position the device distal end 704 in the proper location within the patient's heart. Once the operator is satisfied with the location of the device distal end 704, the sheath control knob 752 can be rotated to pull the sheath 716 proximally and expose the distal end petals of the prosthetic valve. FIGS. 13A and 13B show the inner sheath 716 retracted, which would expose the distal end of the valve (allowing it to expand) and expose the collapsed proximal end of the valve (held in the collapsed configuration by the tethers).

To expand the proximal end of the valve, the tether control lock 734 is unlocked so that the operator may begin to adjust the tether control lever 738. By pushing the tether control lever 738, tension on the tethers are lessened. The reduced tension on the tethers in combination with the inner sheath 716 being retracted, allow the series of distal petals on the prosthetic valve to curl back into their natural shape for positioning. Advantageously, at this point, if the operator decides that the proximal anchor and/or the entire valve has not be positioned as desired, the tethers can be tightened again, causing the proximal anchor to collapse. The inner sheath can then be advanced, fully covering the valve and allowing it to be either repositioned or removed entirely.

Figure 14:
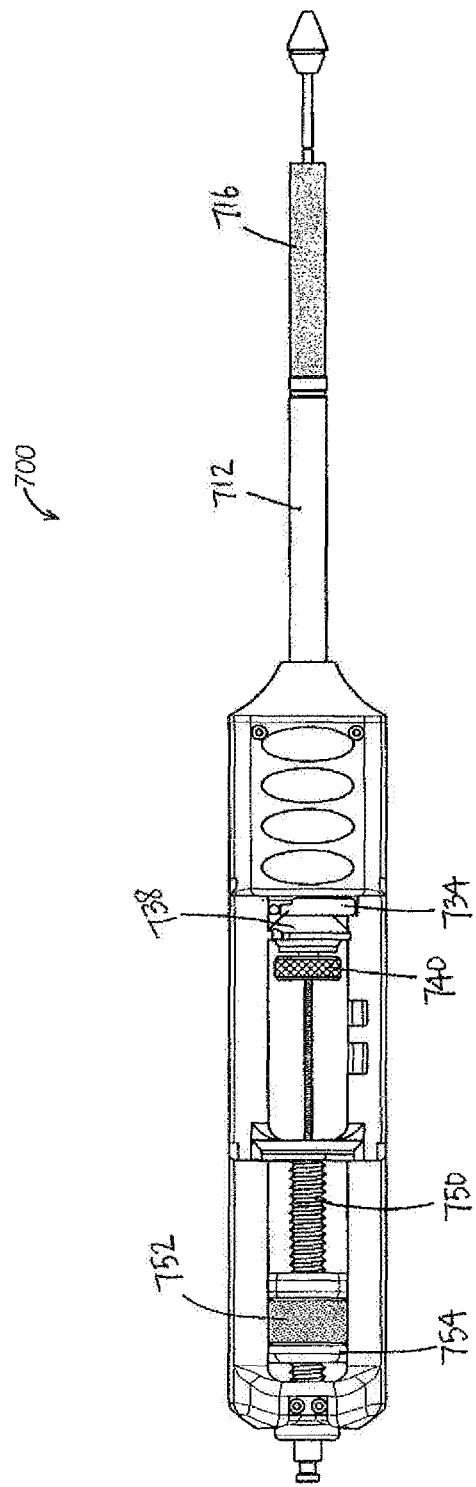
FIG. 14 shows the delivery device of FIG. 11A where a clip maintaining tether tension has been removed.
Figure 15A:
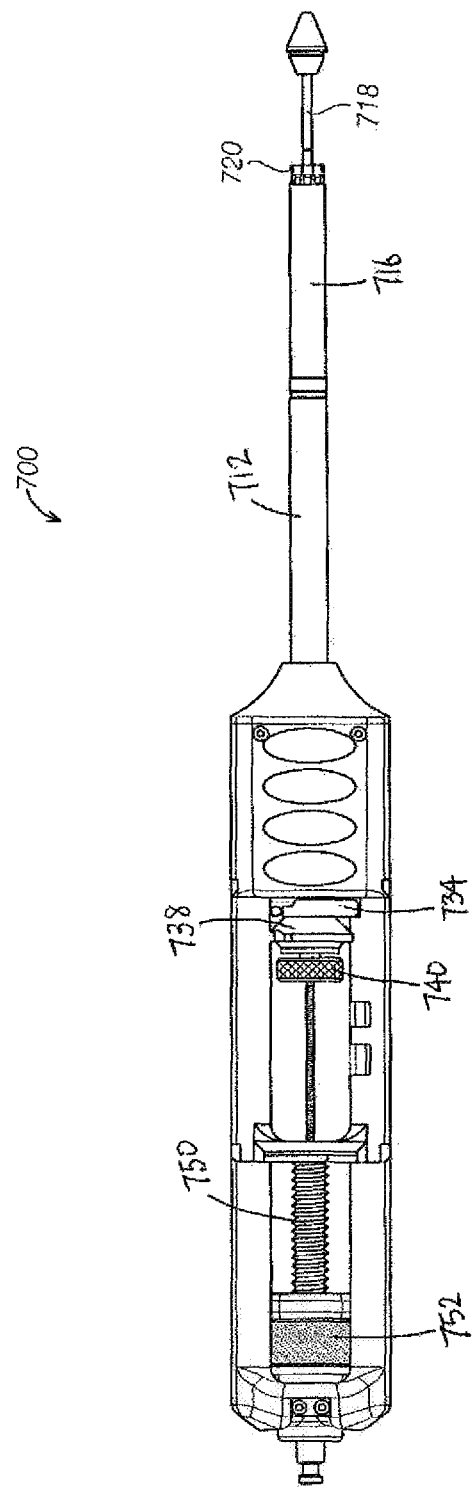
FIG. 15A shows the delivery device of FIG. 11A where a tether ends holder near the distal end is exposed, and tether ends are able to release.
Figure 15B:
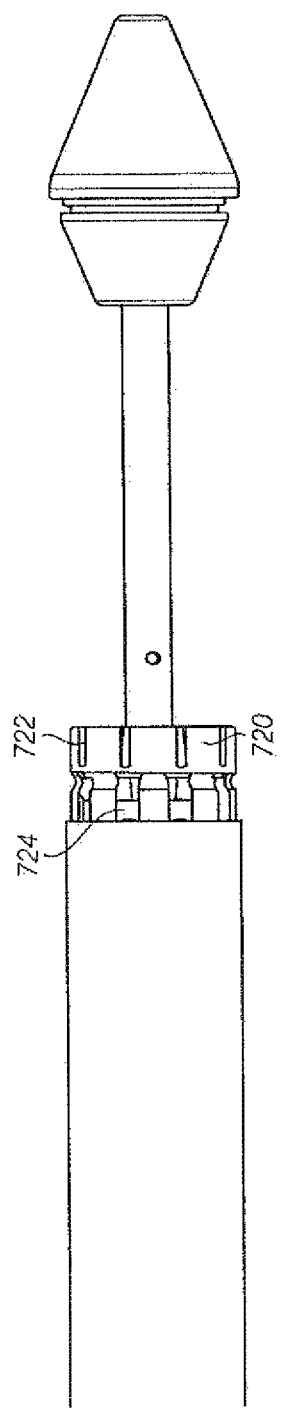
FIG. 15B shows a close-up of the tether ends retainer of FIG. 15A.

Once the positioning of the valve is finalized, the operator can release the valve from the delivery device 700. Referring to FIG. 14, to do so, the clip 754 disposed at the end of a lead screw 750 (shown in FIG. 12A) until now, has function to prevent the inner sheath 716 from retracting too far, may be removed. As shown in FIGS. 15A-15B, this allows the sheath control knob 752 to travel further toward the device proximal end 702 for releasing the tether ends (FIG. 14). Specifically, the clip 754 may be removed to allow the inner sheath 716 to retract to the farthest proximal position possible. Once at the inner sheath 716 is at the farthest proximal position, the tether retaining pockets 724 become exposed, and without the inner sheath 716 to maintain the tether ends within the pockets 724, the proximal tether ends are allowed to pop out of their respective pockets 724 and the proximal side of the prosthetic valve is able to deploy.

Now the entire prosthetic valve has been deployed and the delivery device may be removed. The outer sheath 712 can remain coupled to the incision site thought the outer sheath groove 714 and the purse-string suture. However, once the purse-string sutures are removed, then the entire delivery device may be removed.

In some embodiments, an operator may desired an alternative or additional method for removing the tethers from the proximal anchor (e.g., if the tethers get caught in the anchor and/or don't pop out of the pockets).

Referring to FIGS. 11A and 17, the secondary release knob 740 provides an alternative method of releasing the tethers if the tethers become tangled or fouled up during prosthetic valve loading or deployment. As FIG. 17 shows, the tethers are threaded through the tether control lever 738 past a washer or cushion before travelling distally to where the distal ends will loop around the prosthetic valve. As can be seen in FIG. 17, the secondary release knob 740 is screwed down against the washer or cushion to maintain tension on the tethers. In instances where the operator needs to reload the tethers, the release knob 740 may be used. To use the release knob 740, the operator rotates the knob 740 in the direction that reduces the force on the washer/cushion, thereby releasing tension on the tether ends against a washer. Because there is no need to adjust the secondary release knob 740 unless the operator needs to adjust tangled or stuck tethers, the secondary release knob 740 may be color coated a different color (i.e. red) to alert the operator that this knob should not be adjusted unless absolutely necessary to prevent the operator from inadvertently releasing the tether ends prior to fully loading the prosthetic valve or accidentally deploying the prosthetic valve prior to finding an optimal position for the valve.

Figure 18A:
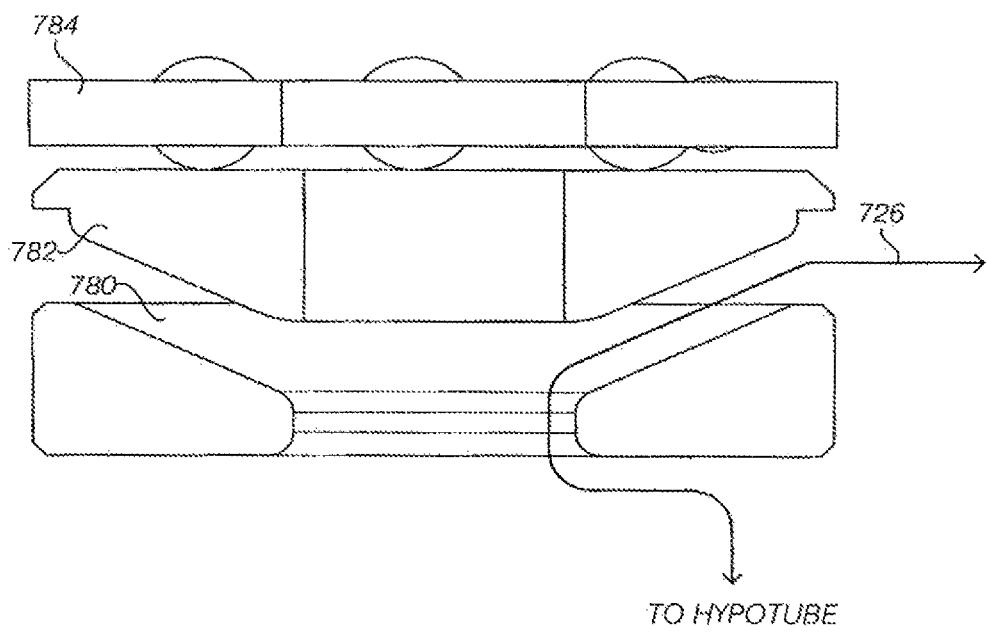
FIG. 18A shows an alternative embodiment of the proximal tether control and retaining feature having a truncated conical washer.
Figure 18B:
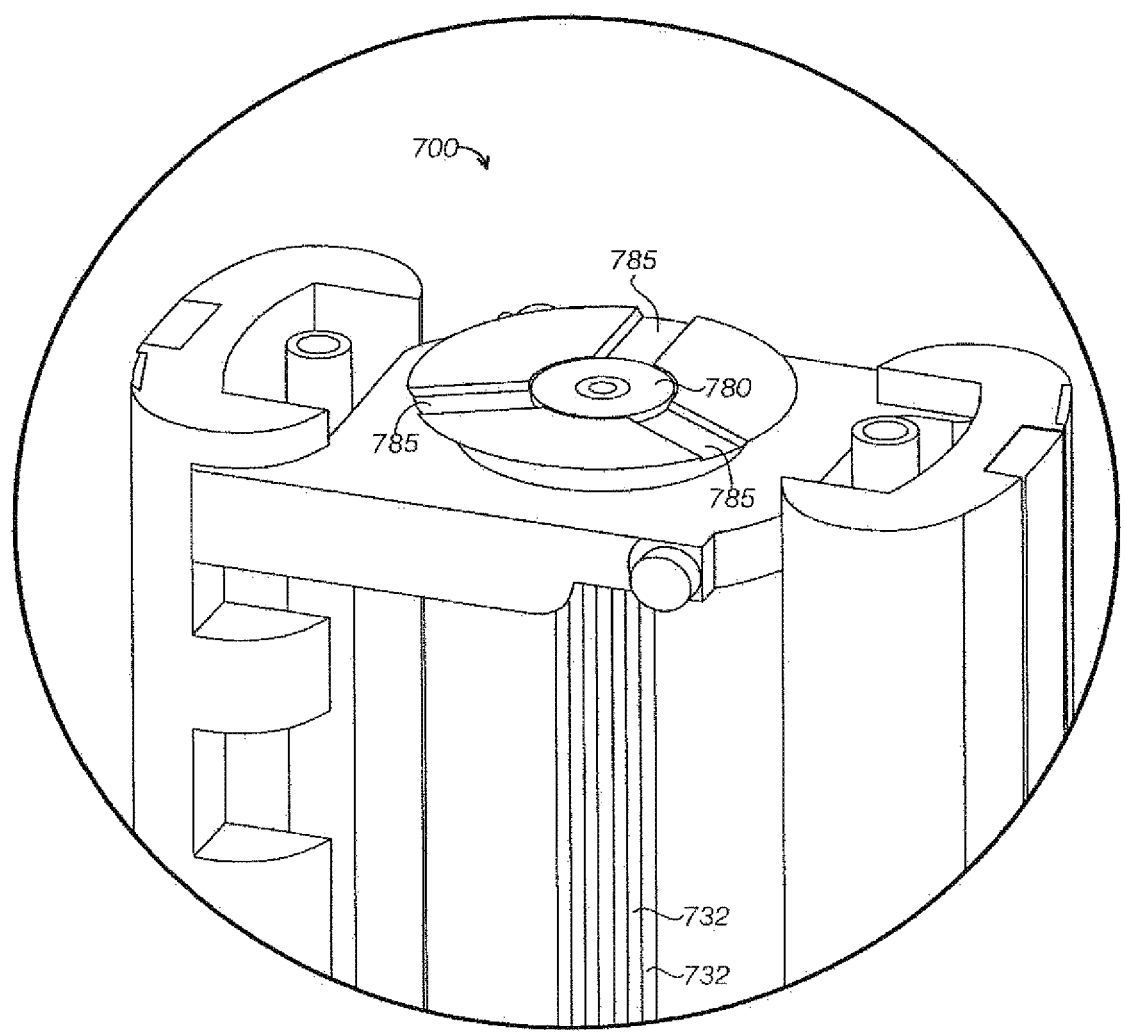
FIG. 18B shows a top portion of the truncated conical washer of FIG. 18A having three channels.

An alternative embodiment of the alternative tether release mechanism is shown in FIGS. 18A and B. Here, a truncated cone 782 and corresponding funnel-shaped washer 780 apply tension to the proximal tether ends. The path that the tether ends take in this configuration has a much more natural angle compared to the approximately ninety degree angle jog that the proximal tether ends must take in the prior configuration described (FIG. 17). In this example, the tethers or sutures are threaded three each into each of the three channels 785. In this alternative configuration, a thrust bearing 784 is used to prevent rotation of the washer 780 when threading the thumb screw 750. In the absence of this feature, when the thumb screw 750 is rotated with a certain amount of force on the tethers 726 and potentially twist the tethers 726 together which could lead to difficulty adjusting the tension on the tethers.

Figure 21A:
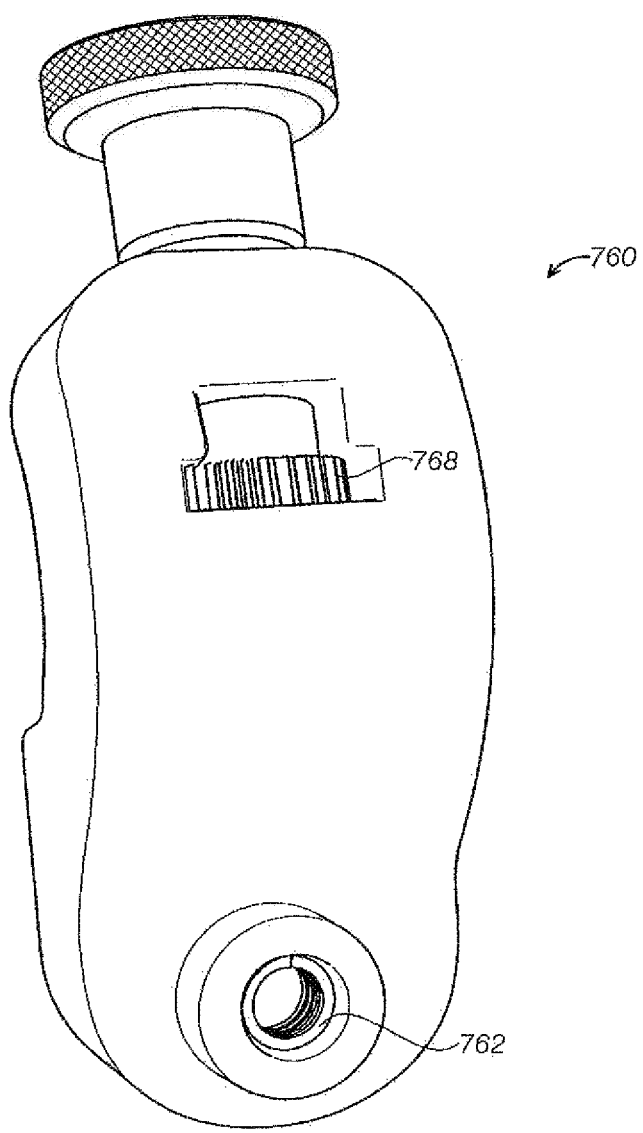
FIG. 21A shows a top view of a grasper.
Figure 21B:
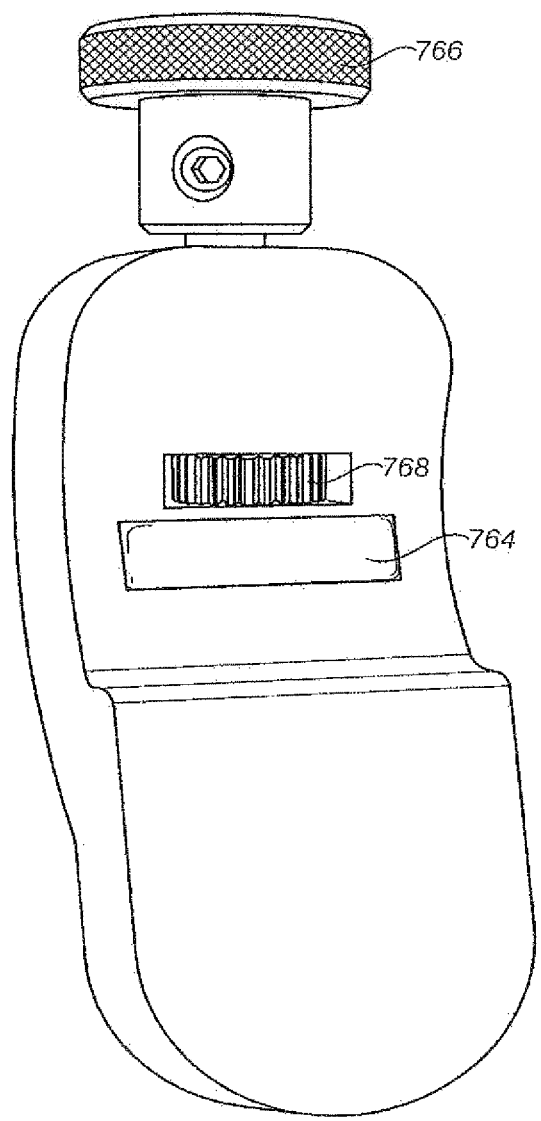
FIG. 21B shows a bottom view of the grasper of FIG. 21A.
Figure 22:
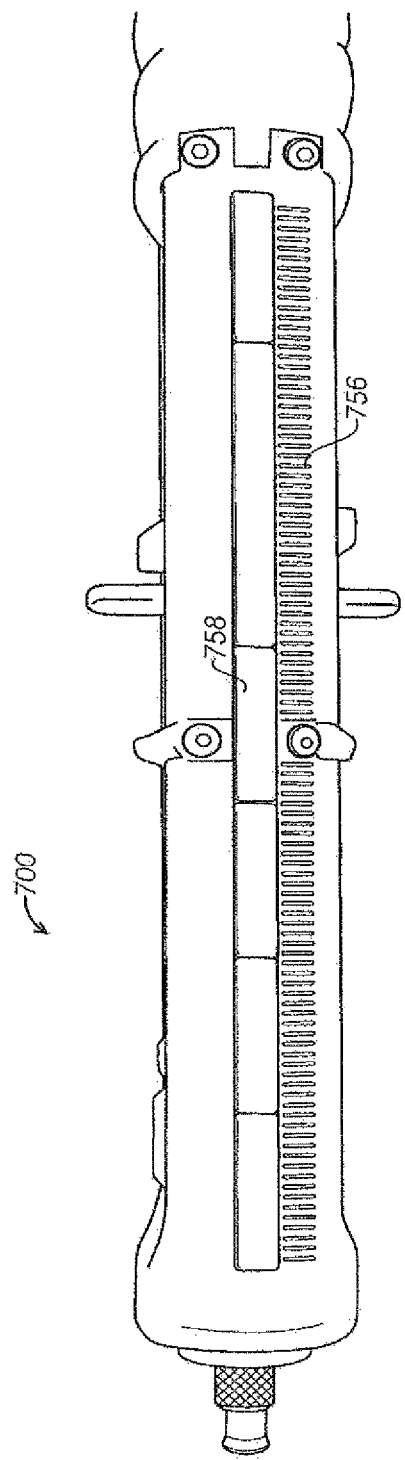
FIG. 22 shows a side view of a handle of a delivery device for mating attachment to a grasper.

In some embodiments, the delivery device 700 also includes a grasper 760 as shown in FIGS. 11A, 21A, and 21B. The grasper 760 allows the operator to adjust the depth with which the device distal end 704 penetrates the patient's heart chamber as well as aids with maintaining the delivery device 700 during use. In general, the grasper 760 includes a grasper coupling aperture 762, grasper magnets 764, and a grasper adjustment knob 766 mechanically coupled to a grasper coupling wheel 768. The grasper 760 generally has an oblong shape. On one end, the grasper 760 includes the grasper coupling aperture 762 and on the opposing end is the grasper adjustment knob 766 coupled to the grasper coupling wheel 768. On its bottom surface is the grasper magnet 764 adjacent to the grasper coupling wheel 768. The grasper coupling wheel 768 is situated in an opening where it is raised above the surface of the grasper. As can be seen from FIG. 22, the delivery device 700 includes a device magnet strip 758 disposed on one side of the device. The device magnet strip 758 may be a single rectangular magnet or a series of individual magnets. In use, the grasper magnets 764 are able to couple to the device magnet strip 758. Adjacent to the device magnet strip 758 are a series of device tracks 756. The device tracts 756 are able to couple to the grasper coupling wheel 768 such that when the operator rotates the grasper adjust knob 766, the teeth of the grasper coupling wheel 768 are able to travel proximally and distally along the device tracks 756. The grasper coupling aperture 762 in this current example is a threaded connection that couples the grasper 760 to a standard VBM arm for supporting and adjusting the delivery device 700. When the grasper 760 is coupled to both the delivery device 700 and a support arm (such as a VBM arm), the operator may adjust the depth of the delivery device distal end 104 within the patient's heart cavity by simply adjusting the grasper adjust knob 766.

Figure 19:
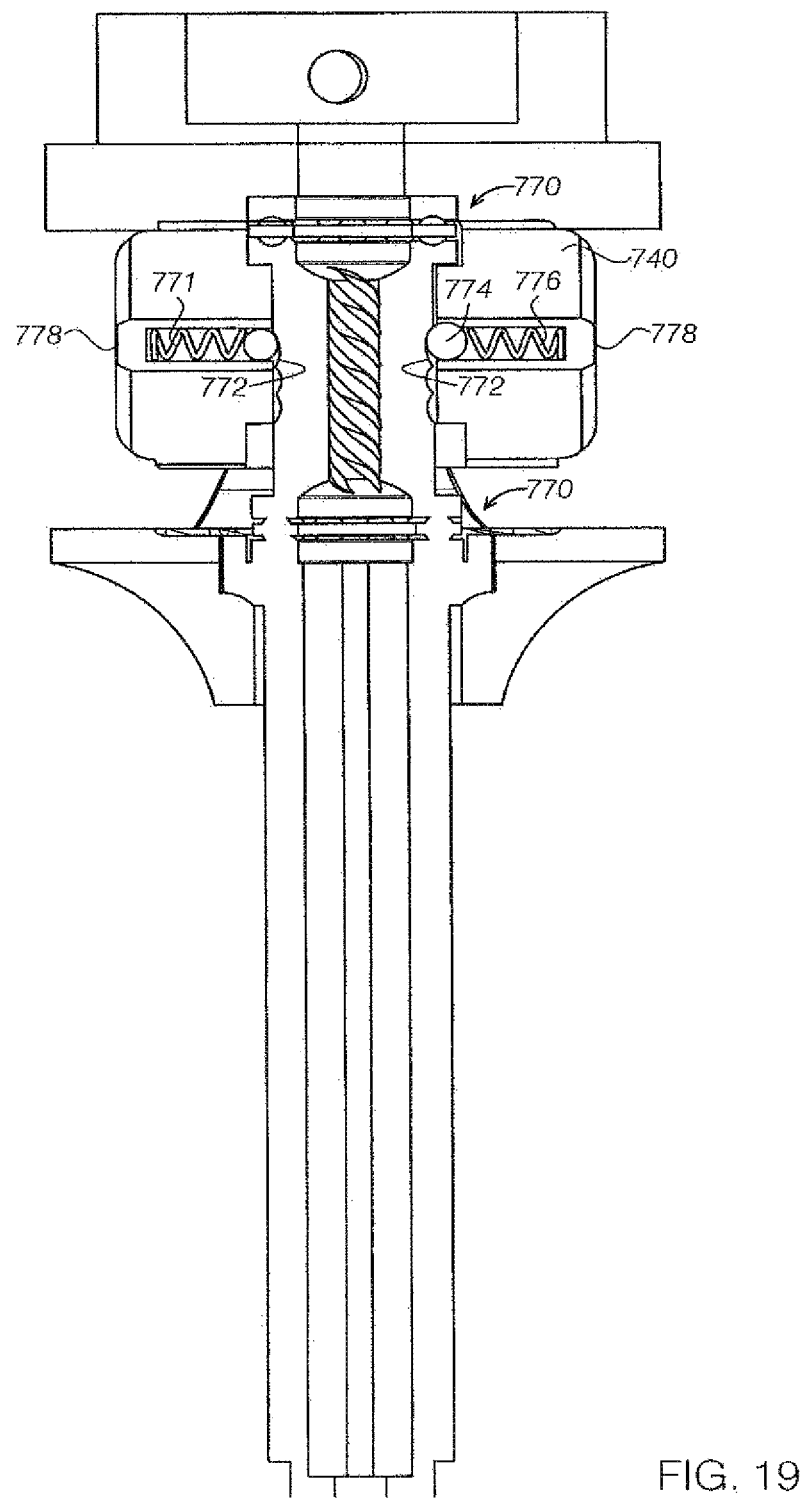
FIG. 19 shows a ratcheting system for maintaining the position of a tether control lever and a secondary release knob.

In some embodiments, the delivery device 700 includes a ratcheting mechanism for preventing back-driving (e.g. slippage) of the tether control lever 738 and the secondary release knob 740. A schematic of the ratcheting mechanism is shown in FIG. 19. FIG. 19 is a cross-section of the secondary release knob 740. The secondary release knob 740 includes a release knob central stem 745 and a release knob center screw 746 contained within. The release knob central stem 745 includes internal features for accommodating the natural outer profile of the turns of the release knob center screw 746. The release knob center screw 746 includes a series of ratcheting teeth 770 at its proximal and distal end within the release knob central stem 745. Disposed on two sides of the release knob central stem 745 are a series of three indentations 772 on each of the sides. The secondary release knob 740 includes two channels 771 situated on opposite sides of each other (180 degrees apart). Within each channel 771 closest to the release knob central stem 745 are identical ball bearings 774. Adjacent to each of the ball bearings 774 are two identical springs 776 and adjacent to the springs on their opposite side are two ratchet actuators 778. The ratcheting mechanism has three possible positions based on which well of the series of indentations 772 the ball bearing 774 is seated. When the ball bearing 774 is in the most proximal well, this places the ratchet mechanism in a position that prevents back-driving of the secondary release knob 740 and the tether control lever 738. When the ball bearing 774 is in the most distal well, this places the ratchet mechanism in a position that previews forward driving of the secondary release knob 740 and the tether control lever 738. Finally, when the ball bearing 774 is in the center position within the series of indentations 772, the secondary release knob 740 and the tether control lever 738 are free to move either distally or proximally along the axis of the release knob center screw 746. In some examples, the operator will pull the actuators 778 to release tension against the ball bearing 774 and adjust the tether control knob 738 to move the ball bearing 776 between the three possible positions. In other examples, the ratchet actuators 778 has two positions. In a first position, the ratchet actuators 778 maintains a force against each ball bearing 774 through the springs 776 to keep ball bearing 776 within the desired indentation 772. In a second position, the operator is able to release the force the ratchet actuator 778 exerts upon the ball bearing 774 and by adjusting the secondary release knob 740, is able to transfer the ball bearing 774 into a different well within the series of indentations 772.

In any of the embodiments herein, the proximal portion of the prosthesis may be expanded before the distal portion. For example, if it is difficult to advance the delivery device far enough into a left ventricle to deploy the distal portion first, or if it is undesirable to deploy the distal portion first against mitral valve anatomical structures (e.g., the chords), the proximal portion can be deployed first. The delivery devices herein can be modified with an outer component that can be axially moved to allow the proximal portion to expand while still radially constraining the distal portion for subsequent expansion.

Figure 23A:
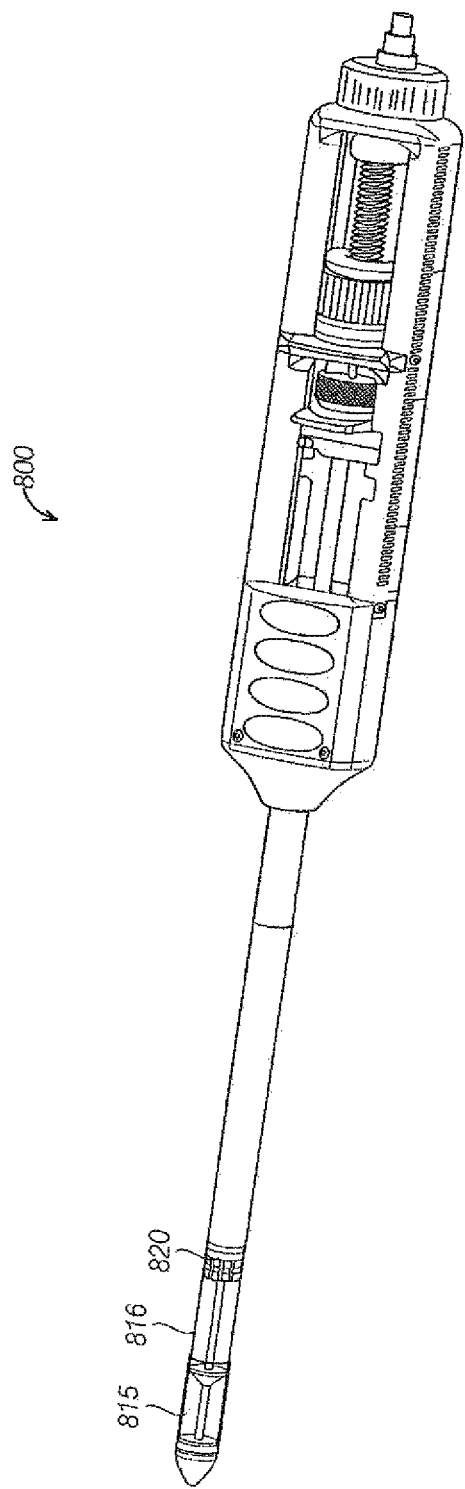
FIG. 23A shows another embodiment of a delivery device.
Figure 23B:
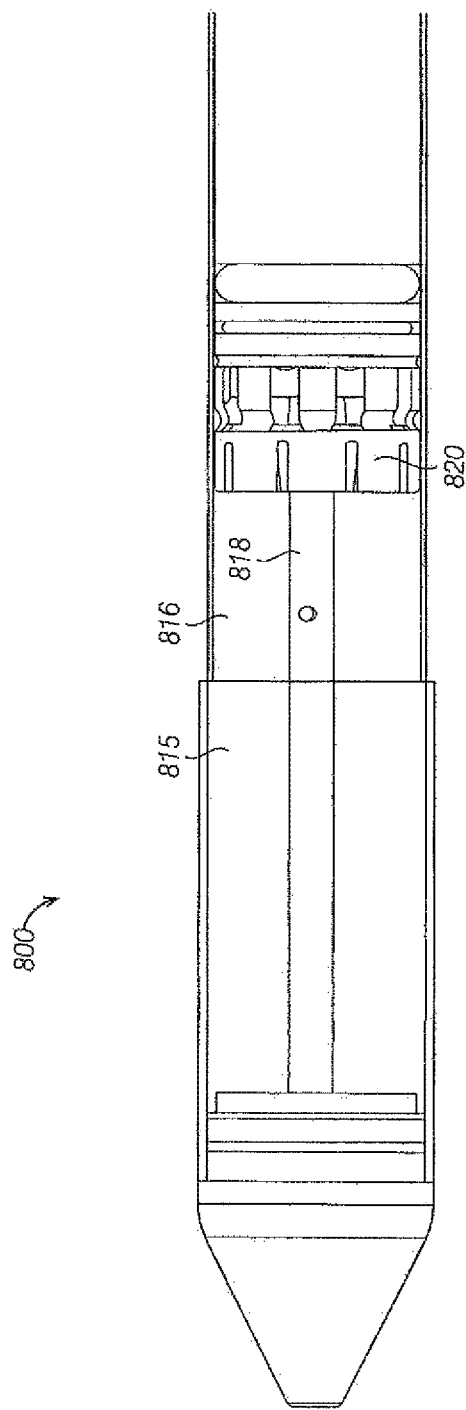
FIG. 23B shows a close up of the distal end of the delivery device of FIG. 23A.
Figure 23C:
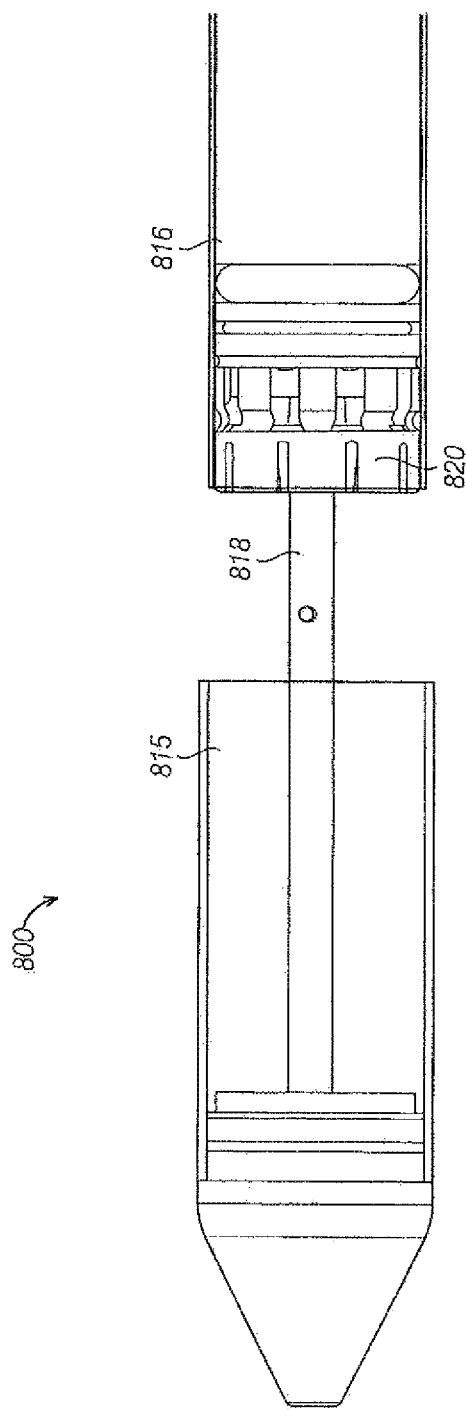
FIG. 23C shows the delivery device of FIG. 23A with a distal inner sheath and a proximal inner sheath moving away from one another.
Figure 23D:
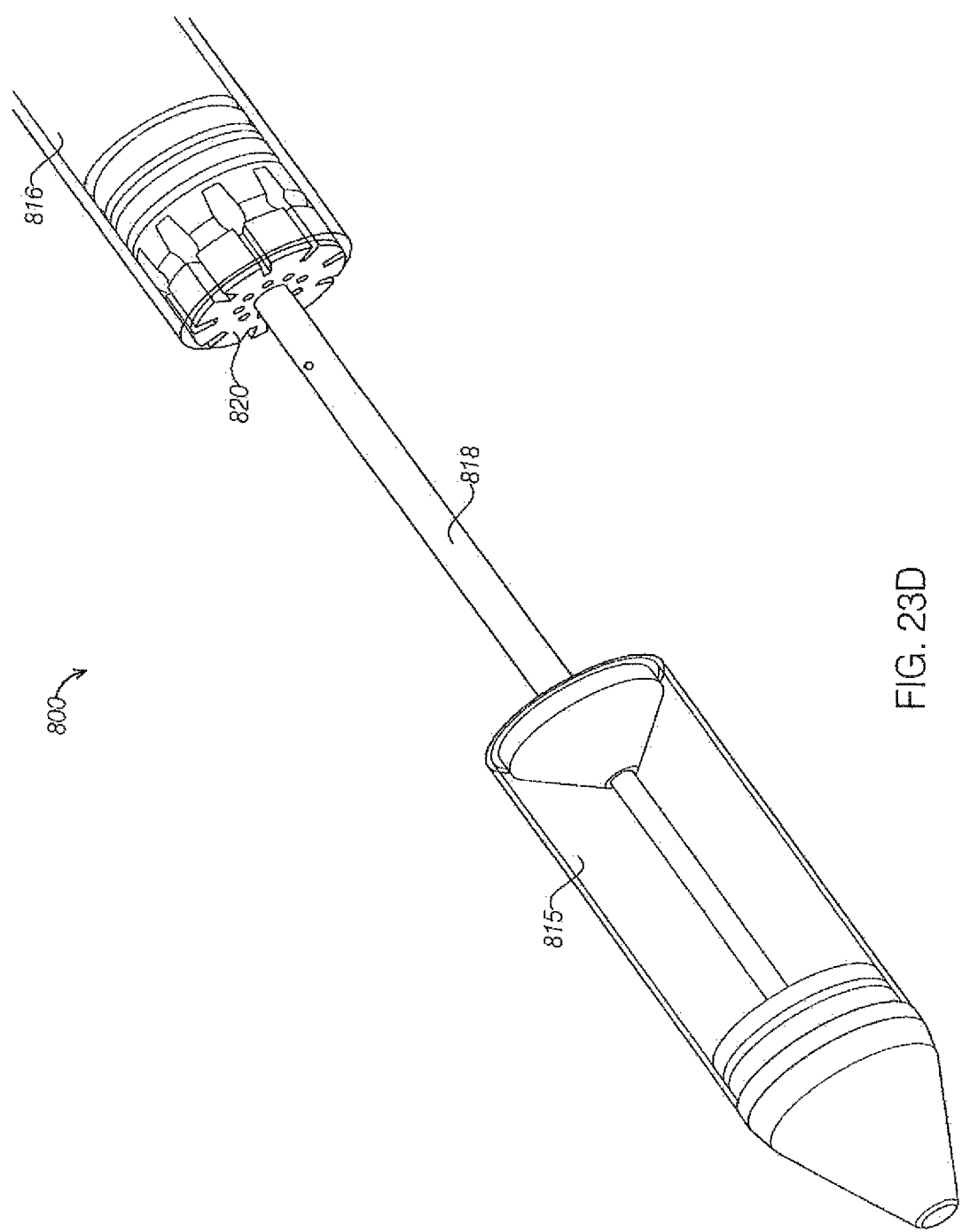
FIG. 23D shows the distal inner sheath and the proximal inner sheath of FIG. 23C moving farther from one another.
Figure 23E:
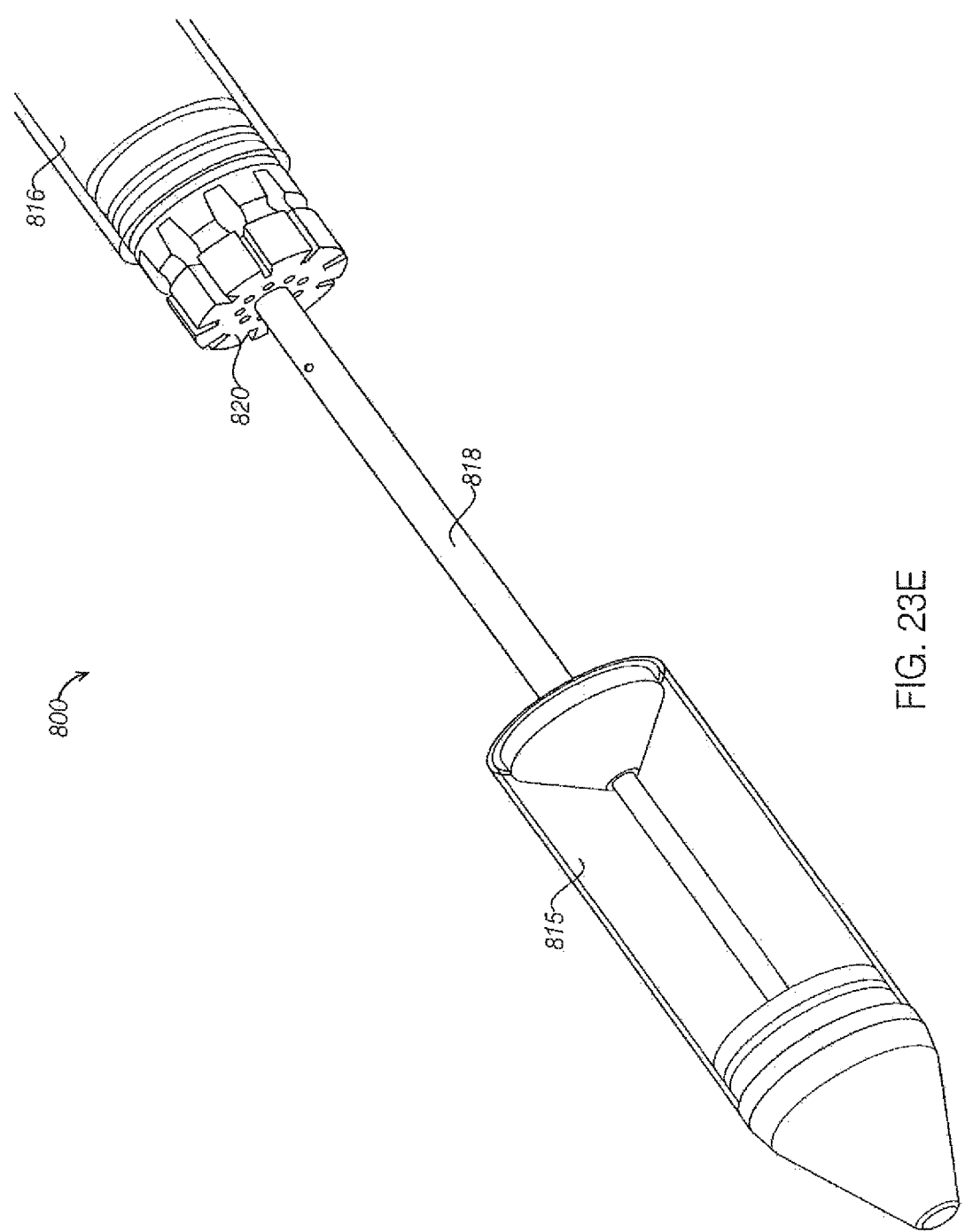
FIG. 23E shows a tether retainer becoming exposed after the proximal inner sheath has been fully further in the proximal direction relative to FIG. 23D.
Figure 23F:
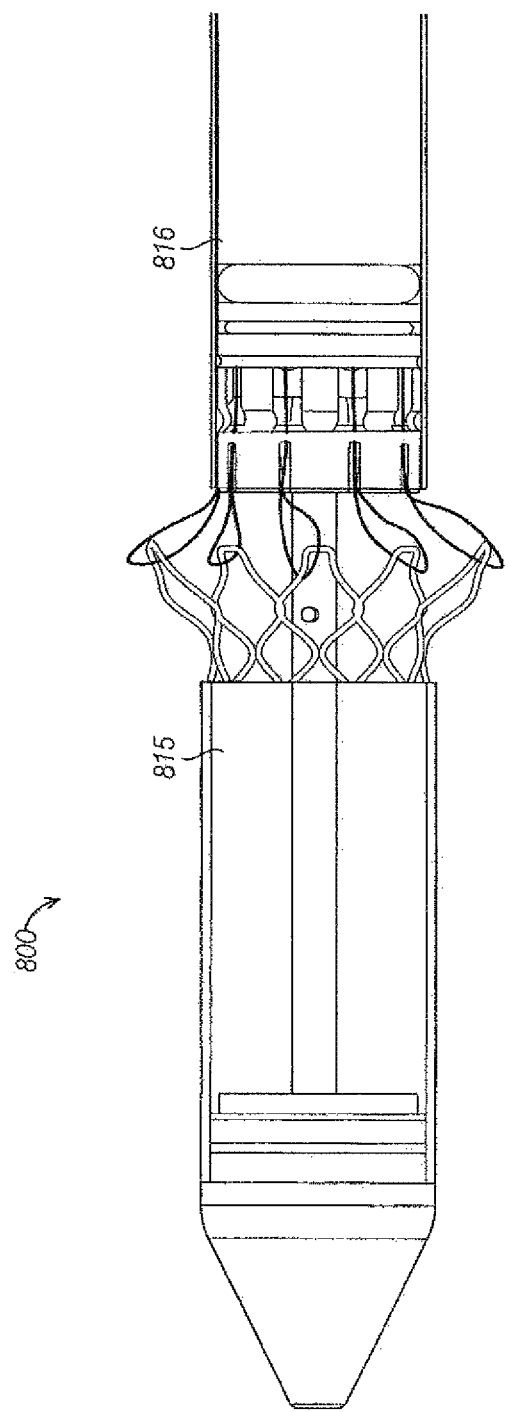
FIG. 23F shows proximal ends of a prosthetic valve deployed but still coupled to a series of tethers of the delivery device of FIG. 23A.
Figure 23G:
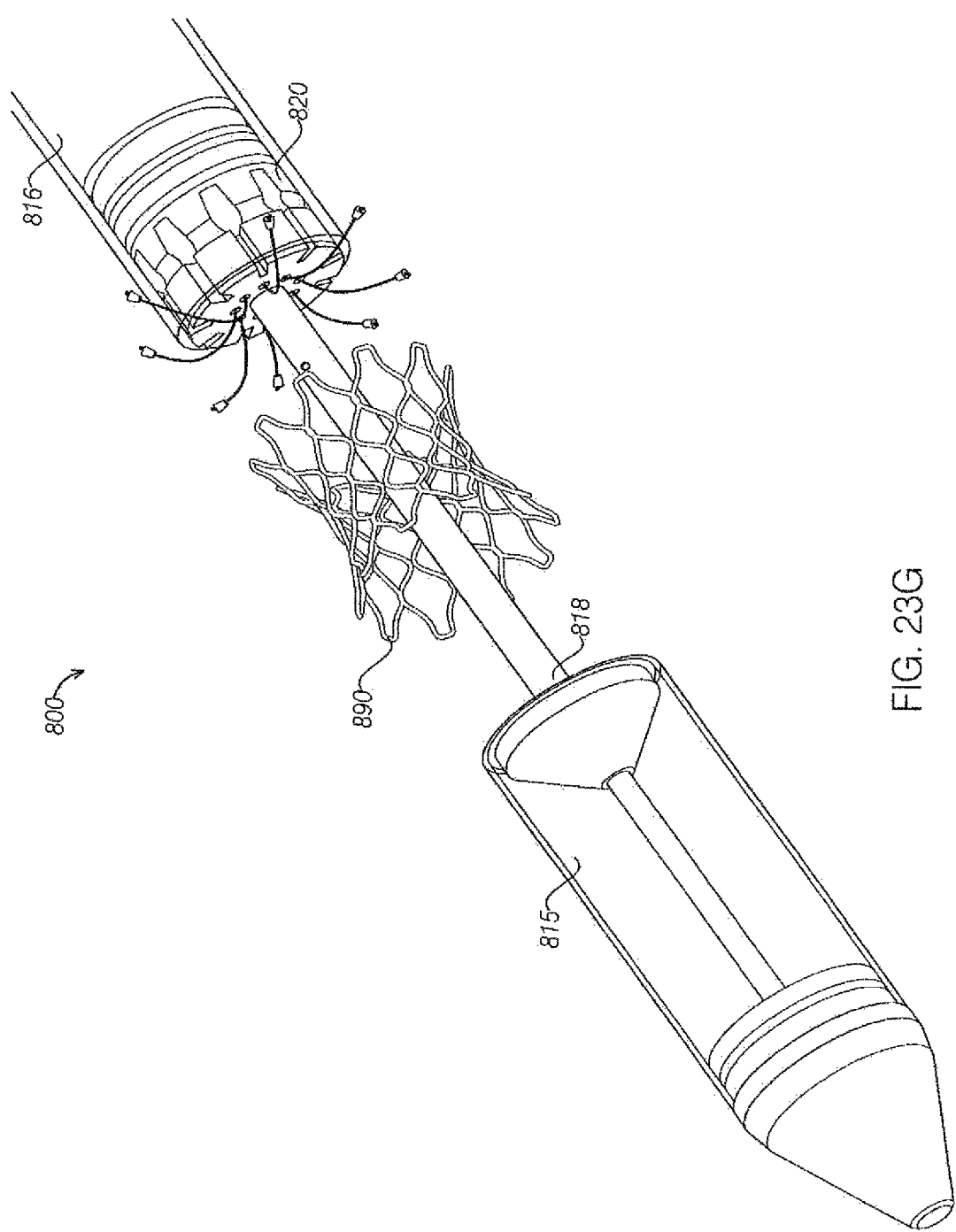
FIG. 23G shows the prosthetic valve fully deployed and uncouple to the tether ends of the delivery device of FIG. 23A.

Turning to FIGS. 23A-G, another embodiment of the mitral valve replacement delivery device 800, is shown. The delivery device 800 shares many of the same features as the delivery devices already described, and thus, features that function the same will not be redundantly described, unless required for clarity. The major difference between the delivery devices already described and the delivery device 800 is that the previously described delivery devices, the distal end petals of the prosthetic valve are deployed first followed by the proximal end petals, while for the delivery device 800, the proximal end petals are deployed first. The delivery device 800 has a device proximal end 802 and a device distal end 804. The delivery device 800 includes two inner sheaths, a distal inner sheath 815 and a proximal inner sheath 816. The distal inner sheath 815 is able to telescope over the distal end of the proximal inner sheath 816 (FIGS. 23A and B). FIGS. 23 C and D show how the proximal inner sheath 816 may be extended and retracted in conjunction with the distal inner sheath 815. Similar to the previous delivery devices, the delivery device 800 includes a tether retainer 820, where the tether retainer 820 is stationary along the centrals stem 818. The prosthetic valve is held in the same manner and orientation as in the previous delivery devices.

Once the prosthetic valve has been coupled to the tethers and the tether ends maintained with the tether retainer 820, the tether control lever 838 may be pulled proximally to tension the proximal petals of the prosthetic valve to close the petals about a central stem 818. The distal end petals of the prosthetic valve may then be forced into a closed position by further pushing the proximal distal sheath 816 distally so that it eventually covers the entire prosthetic valve. Once the entire prosthetic valve has been collapsed, the distal inner sheath 815 may cover a portion of the proximal inner sheath 816. The distal inner sheath 815 is controlled by a distal inner sheath controller 819, which is able to retract and extend the distal inner sheath 815. At its most distal position, the distal inner sheath 815 abuts the nosecone 806. Once the collapsed prosthetic valve is within the distal inner sheath, the proximal inner sheath 816 may be retracted proximally.

To release the prosthetic valve, tension on the tethers may be relaxed. As FIGS. 23E and F show, the distal and proximal inner sheaths 815 and 816 may be positioned to expose the proximal end petals of the prosthetic valve first. This is done by pulling the proximal inner sheath 816 slightly in the proximal direction while also extending the distal inner sheath 815 in the distal direction to first expose the proximal petals. Once the proximal end petals of the prosthetic valve are fully open and positioned, the operator may move the distal inner sheath 815 distally to expose the distal end petals of the prosthetic valve, where the distal petals will naturally curl/flair out to their natural state once the constriction by the distal inner sheath 815 has been removed. The proximal inner sheath 816 may be further retracted to expose the tether retainer 820 so that the tether pockets containing the tether ends are exposed and the tether distal ends may pop from each respective pocket. The delivery device 800 may also include an outer sheath for initially positioning the device within the patient's heart.

Figure 24A:
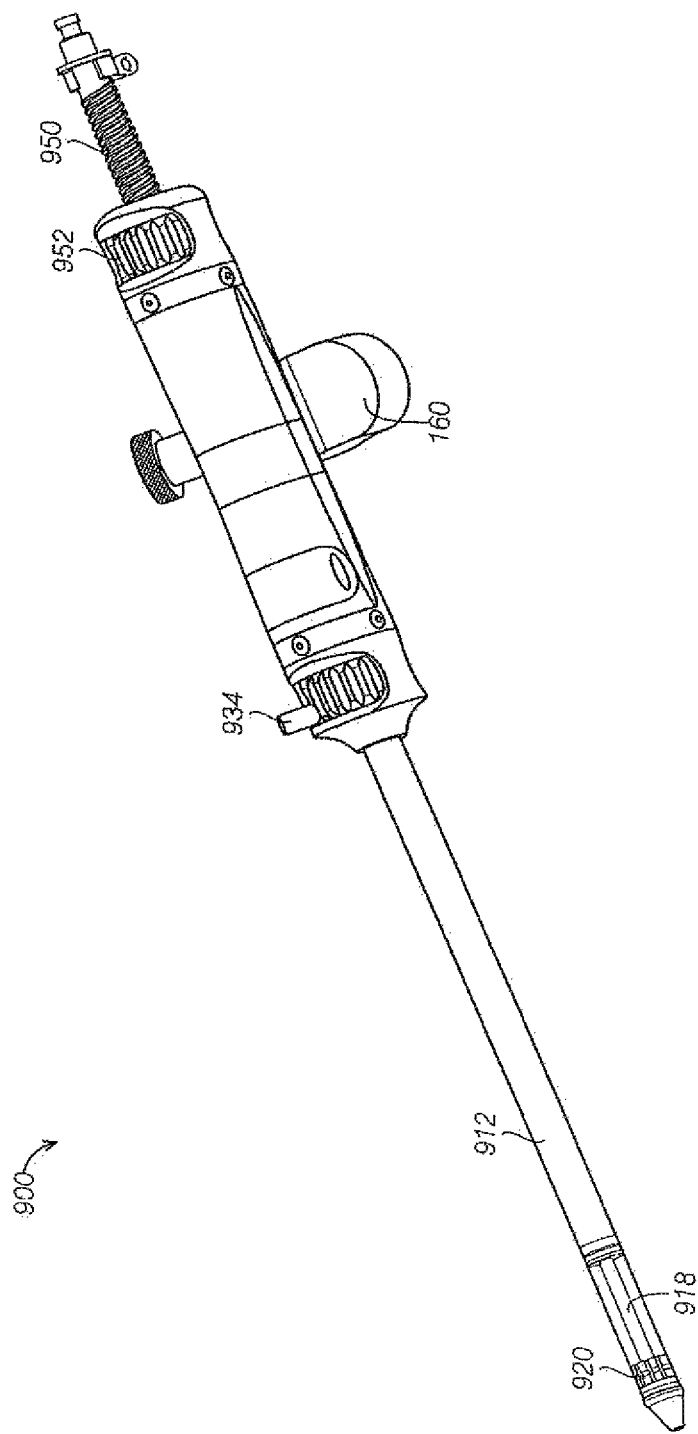
FIG. 24A shows another embodiment of a delivery device.
Figure 24B:
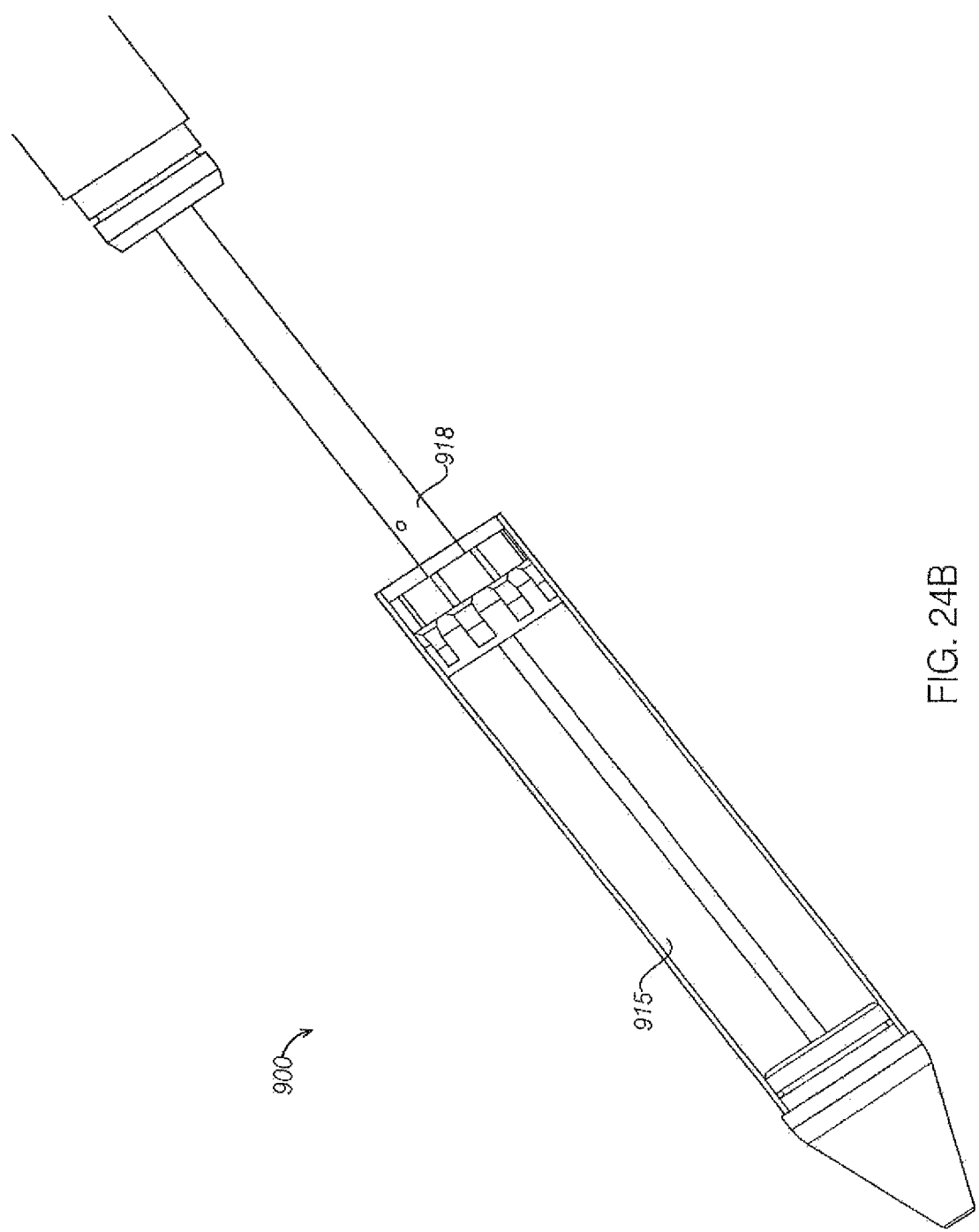
FIG. 24B shows a distal end inner sheath of the delivery device of FIG. 24A partially extended in the distal direction.

Yet another embodiment for prosthetic valve delivery, a delivery device 900, can be seen in FIG. 24A-24F. The delivery device 900 also release the proximal end petals of the prosthetic valve first. The delivery device 900 as shown in FIG. 24A uses a slightly different mode of maintaining the tether for the prosthetic valve compared to delivery device 800. Similar to delivery device 800, the delivery device 900 includes a shorter distal sheath 915 that abuts a nosecone 906 at a device distal end 904. The delivery device 900 includes a distal sheath 915 that may extend and retract with the use of a sheath controller 952 (FIG. 24B). The delivery device 900 further includes a central stem 918. Unlike in previous configurations, the central stem 918 here further includes a series of nesting tubes. In this particular configuration, nine nesting tubes 933 are arranged around a center core that runs to the nosecone 906. The center core houses a guidewire known in the catheter arts. Instead of a tether control lever, the delivery device 900 includes a tether control knob 938, where the tether control knob 938 functions to increase, decrease, or maintain tension on the tether ends. Similar to the other delivery devices, the proximal ends of the tethers are maintained at the tether control knob 938. In one example, each tether runs from the tether control knob 938 to a nesting tube 933 until it reaches the tether retainer 920. Each tether exits its respective nesting tube at a distal location and threads into a corresponding tether retaining aperture 923, where each tether travels the length of the tether retainer 920 and exits the tether retaining apertures 923 at its proximal end. From there, each tether distal end may be introduced into corresponding tether pockets 924 and tether slots 922.

To load a prosthetic valve, the free tether ends near the distal end of the delivery device 900 are looped around the distal end petals of the prosthetic valve. Once the tethers have been coupled to the prosthetic valve, the tether control knob 938 may place tension on the distal end petals through adjusting the tether control knob 934 and pull them close toward the central stem 918. In delivery device 900, the distal sheath 915 may be pulled back proximally along a central stem 918. When the distal end petals have been so tensioned as to pull them straight, the distal end sheath 915 may be extended proximally to cover the distal end petals. Further retracting the distal end sheath 915 will begin to cover the proximal end petals of the prosthetic device. The collapsed prosthetic valve and the tether retainer 920 are eventually completely maintained within distal inner sheath 915. The sheath control knob 952 adjusts the position of the distal inner sheath 915 through lead screw 950. The distal sheath 915 abut the nosecone 906.

For deploying the prosthetic valve, the distal inner sheath 915 may be extended distally relative to the tether retainer 920 by adjusting the sheath control knob 952. When this occurs, the proximal end petals are exposed. Because the distal inner sheath 915 was the only thing keeping the proximal petals in a straightened configuration, once this confinement is removed, the proximal end petals will relax and curl to their natural shape (FIG. 24C). Once the proximal end petals have been place in an optimal location within the patient's heart, the distal inner sheath 915 may be further extended distally in conjunction with relaxing tension on the tether ends through adjusting the tether control knob 938 which allow the distal end petals to relax and expand (FIG. 24D). The distal inner sheath 915 may be further advanced distally such that the pockets of the tether retainer 920 are exposed and the tether ends are allowed to become uncoupled to the tether retainer 920 (FIG. 24E). Finally the tether ends may be tensioned so that they are pulled free from the prosthetic device completely (FIG. 24F), where now the delivery device may be removed.

Figure 10:
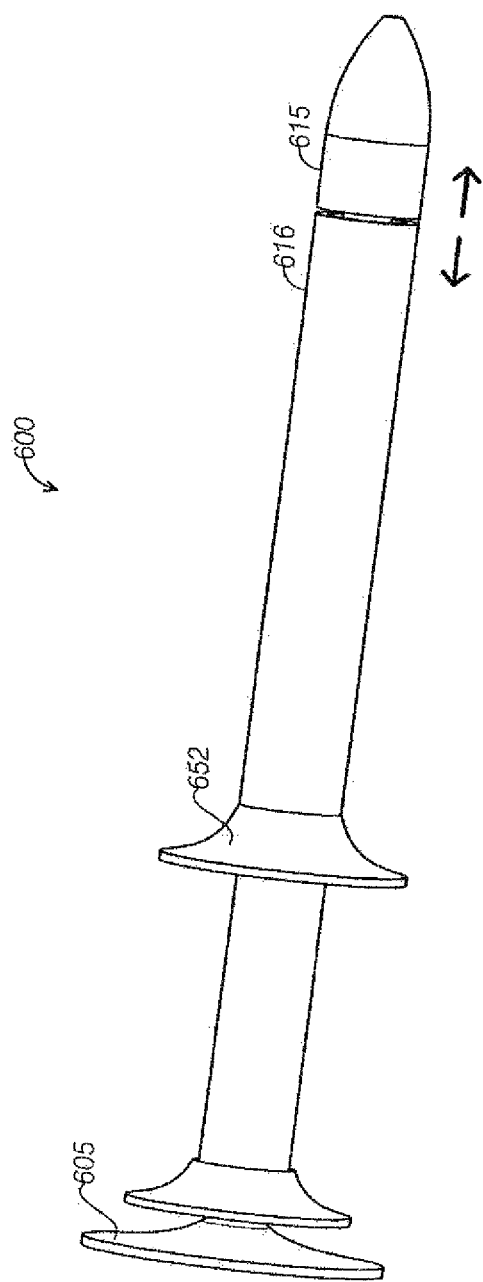
FIG. 10 shows another embodiment of a prosthetic valve delivery device.

FIG. 10 shows another exemplary delivery device 600 that is configured to expand the proximal portion before the distal portion. The central assembly of delivery device includes an expansion control member, and in other embodiments herein. However, in this example, the expansion control member is positioned and configured to maintain the distal portion in a collapsed configuration. The proximal portion is allowed to freely expand upon retraction of the outer sheath. In use, the sheath control handle 652 is retracted in the proximal direction (as shown by the arrow), causing proximal sheath 616 to be withdrawn proximally. This causes the proximal portion of the expandable anchor to self-expand. The distal portion of the expandable anchor is still maintained in a collapsed delivery configuration radially within the distal sheath 615. To expand the distal portion of the anchor, sheath control handle 652 is advanced distally, causing distal sheath 615 to be distally advanced (as shown by the arrow) past the distal portion of the expandable anchor. This causes the distal anchor portion to self-expand. Thus, device 600 is configured such that a proximal portion of the expandable anchor is expanded before the distal portion.

The device in FIG. 10 can similarly include any of the additional restraining elements (e.g., tethers) described herein to further control the expansion of either the proximal or distal anchor portions.

In all the embodiments that allow for deployment of the proximal end petals of the prosthetic valve, an outer sheath may be present for maintaining the incision site similar to what was described for the delivery device that provided deployment of the prosthetic valve distal end petals first.

For any of the delivery devices described herein, certain portions of the delivery device may be composed of transparent or see-through material. This may aid the operator with visualizing what is occurring to the tether lengths and/or prosthetic valve while held within the inner and/or outer sheath.

One or more tethers or suture loops may or may not be included in any of the embodiments herein. For example, any of the restraining elements herein may be used in system that utilizes tethers, but they may also be used in devices without tethers (or tethers).

Aspects of the delivery devices and methods may be combined with aspects of the delivery devices and methods described in U.S. patent application Ser. No. 14/677,320, U.S. Pat. No. 8,870,948, or International Patent Application filed May 13, 2016 and titled "REPLACEMENT MITRAL VALVES," the entirety of which is incorporated by reference herein.

Although described herein for use with a mitral valve prosthetic, the delivery systems described herein can be used with a variety of different implantable devices, including stents or other valve prosthetics.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of delivering a prosthetic mitral valve into a patient, comprising:
    extending a delivery device into a heart with the prosthetic mitral valve collapsed within a sheath of the delivery device;
    pulling the sheath proximally to expose at least a distal anchor of the prosthetic mitral valve, thereby enabling the distal anchor to self-expand to an expanded annular configuration on a first side of the mitral valve annulus;
    pulling the prosthetic mitral valve proximally to seat the distal anchor in the expanded annular configuration against the mitral valve annulus;
    loosening a plurality of tethers of the delivery device so as to enable a proximal anchor of the prosthetic mitral valve to self-expand to an expanded annular configuration on a second side of the mitral valve annulus;
    pulling the sheath further proximally to withdraw the tethers from the proximal anchor; and
    removing the delivery device from the heart.

2. The method of claim 1, wherein the step of pulling the sheath further proximally releases distal ends of the tethers.

3. The method of claim 1, further comprising releasing a proximal end of at least one of the tethers if a distal end of the at least one tether becomes tangled.

4. The method of claim 1, wherein distal ends of the tethers are positioned within pockets of the delivery device, and the step of pulling the sheath further proximally releases the distal ends of the tethers from the pockets.

5. The method of claim 4, wherein the distal ends of the tethers include enlarged features configured to fit within the pockets.

6. The method of claim 5, wherein the enlarged features are cones or spheres.

7. The method of claim 1, wherein the expansion of the proximal anchor causes the proximal anchor to move towards the distal anchor and to capture tissue of the mitral valve annulus between the proximal anchor and the distal anchor.

8. The method of claim 1, further comprising, prior to the step of pulling the sheath further proximally:
    tightening the plurality of tethers to re-collapse the proximal anchor;
    moving the distal anchor to a new position against the mitral valve annulus; and
    re-loosening the plurality of tethers so as to enable the proximal anchor to self-expand to the expanded annular configuration on the second side of the mitral valve annulus, the expansion of the proximal anchor causing the proximal anchor to move towards the distal anchor and to capture tissue of the mitral valve annulus between the proximal anchor and the distal anchor.

9. The method of claim 1, wherein prior to loosening the plurality of tethers of the delivery device, the plurality of tethers are looped around the proximal anchor.

\* \* \* \* \*